(12) United States Patent
Moore

(10) Patent No.: US 8,377,130 B2
(45) Date of Patent: Feb. 19, 2013

(54) SPONDYLOLISTHESIS CORRECTION APPARATUS AND METHOD

(76) Inventor: Mark R. Moore, Westlake, LA (US)

( * ) Notice: Subject to any disclaimer, the term of this patent is extended or adjusted under 35 U.S.C. 154(b) by 189 days.

(21) Appl. No.: 12/799,775

(22) Filed: Apr. 30, 2010

(65) Prior Publication Data

US 2011/0270257 A1 Nov. 3, 2011

(51) Int. Cl.
*A61F 2/44* (2006.01)
*A61F 2/46* (2006.01)
(52) U.S. Cl. .................... 623/17.11; 606/86 R
(58) Field of Classification Search .... 623/17.11–17.16; 606/86 R, 87, 99
See application file for complete search history.

(56) References Cited

U.S. PATENT DOCUMENTS

| | | | |
|---|---|---|---|
| 3,486,505 A | 12/1969 | Morrison | |
| 4,714,469 A | 12/1987 | Kenna | |
| 4,863,476 A | 9/1989 | Shepperd | |
| 5,601,556 A | 2/1997 | Pisharodi | |
| 6,086,589 A | 7/2000 | Kuslich et al. | |
| 6,126,660 A | 10/2000 | Dietz | |
| 6,159,212 A | 12/2000 | Schoedinger, III et al. | |
| 6,251,111 B1 | 6/2001 | Barker et al. | |
| 6,491,695 B1 | 12/2002 | Roggenbuck | |
| 6,533,791 B1 | 3/2003 | Betz et al. | |
| 6,582,431 B1 | 6/2003 | Ray | |
| 6,679,915 B1 | 1/2004 | Cauthen | |
| 6,755,841 B2 | 6/2004 | Fraser et al. | |
| 6,899,716 B2 | 5/2005 | Cragg | |
| 6,921,403 B2 | 7/2005 | Cragg et al. | |
| 7,014,633 B2 | 3/2006 | Cragg | |
| 2006/0009767 A1 | 1/2006 | Kiester | |

*Primary Examiner* — Kevin T Truong
*Assistant Examiner* — Christian Sevilla
(74) *Attorney, Agent, or Firm* — Schultz & Associates, P.C.

(57) ABSTRACT

An apparatus and method are provided that allow for the realignment and stabilization of adjacent vertebrae. An implant of this invention both repositions adjacent vertebrae and remains in situ to maintain the new position. The implant has two halves which are interlocked such that they can slide horizontally with respect to each other. Movement of the implant halves and their respective positions are controlled by set screw within the implant. The implant includes radial anchors which fit into alignment slots made in the misaligned vertebra by the disclosed method. The set screws are used to advance the halves of the implant which in turn move the misaligned vertebrae back into correct positions. The correct position of the vertebrae is locked in place through a nut and a plate.

20 Claims, 22 Drawing Sheets

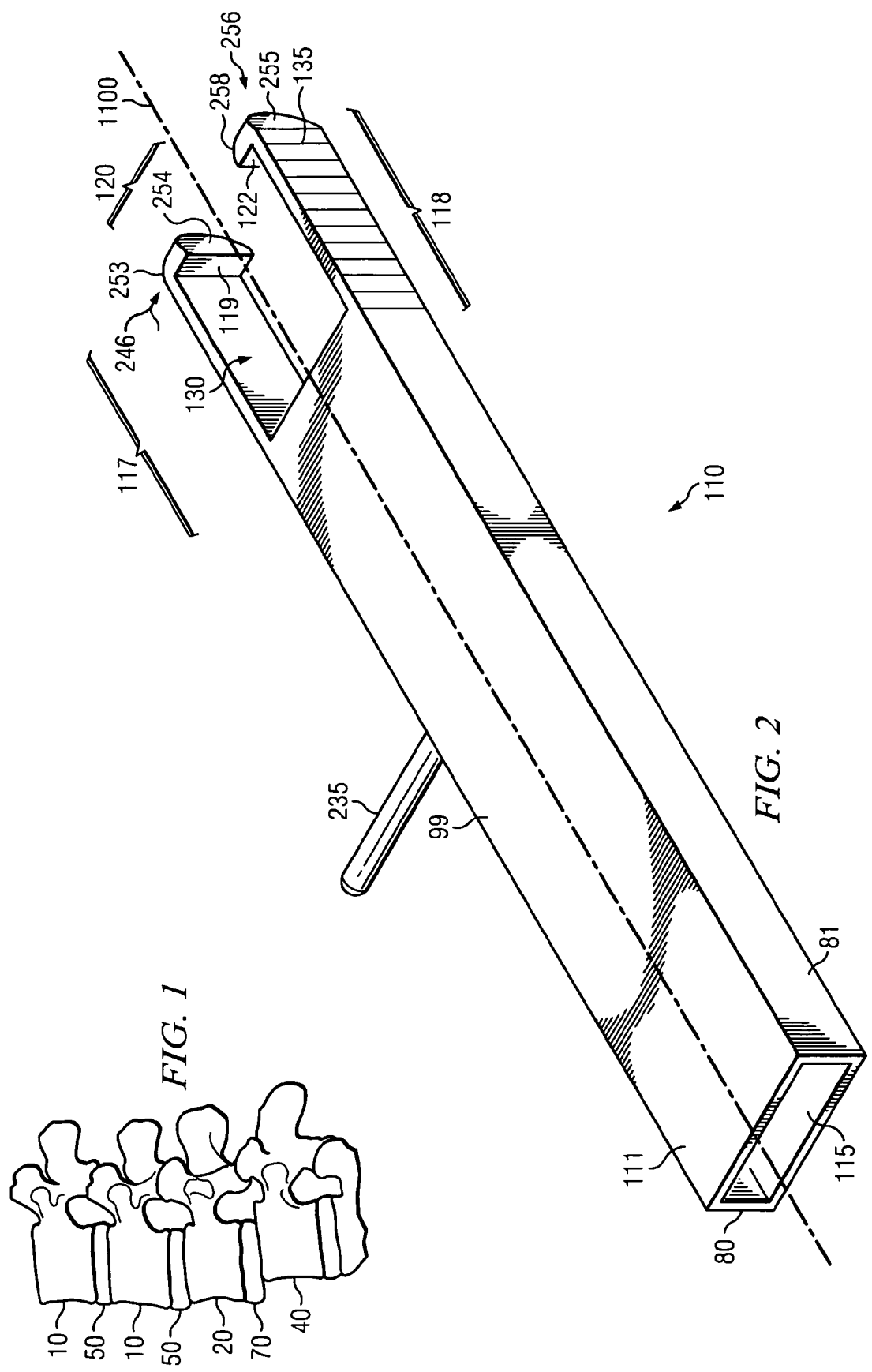

SPONDYLOLISTHESIS CORRECTION APPARATUS AND METHOD

CROSS-REFERENCE TO RELATED APPLICATIONS

This application claims priority to U.S. application Ser. No. 11/821,717 filed Jun. 25, 2007, entitled "Spondylolisthesis Correction Apparatus and Method."

FIELD OF INVENTION

The present inventions relates generally to the correction of spondylolisthesis and other spinal column injuries or deformities in the fields of neurosurgery and orthopedics. More specifically, the invention is used for the stabilization of repositioned vertebral bodies.

BACKGROUND OF THE INVENTION

Spondylolisthesis is a medical condition in which one vertebra slips forward in relation to an adjacent vertebra usually in the lumbar region of the spine. This condition can cause symptoms that include pain in the low back, thighs, and/or legs, muscle spasms, weakness, and/or tight hamstring muscles while in some cases only radiographic imaging reveals the condition.

To correct this condition and other similar conditions of vertebral dislocation, the only effective long-term curative treatment is reconstructive surgery and fusion of the affected vertebra to its adjacent neighbor. Vertebral fusion is generally accomplished by fixing apparatus to and between vertebrae. In addition to the stabilization and correction of spondylolisthesis, other spinal conditions may be: stabilization of fractures, correction of spinal deformities (e.g. scoliosis, kyphosis), stabilization and correction of degenerative spinal lesions and narrow spinal canal, reconstruction after tumor resection, and secondary spinal surgery.

The novel method and implant discussed herein allows for the correction of spondylolisthesis by movement of the vertebrae into better alignment while maintaining stabilization of the vertebrae in the new position in order for the spinal fusion to be completed by ossification. Specifically, the implant is used to move the vertebrae into a post-surgical position and keep the vertebrae in the post-surgical position during the ossification process.

Roggenbuck in U.S. Pat. No. 6,491,695 discloses the use of an apparatus and method for aligning vertebrae which involves creating a helical threaded surface in endcaps of the vertebrae and then threading a positioning device into position to align the vertebrae. Once the vertebrae are positioned, the positioning device is removed and an implant is inserted to maintain the vertebrae in position.

Ray in U.S. Pat. No. 6,582,431 discloses the use of an expandable non-threaded spinal fusion device which requires the vertebrae to be moved into correct position before the device can be inserted and implanted.

Betz in U.S. Pat. No. 6,533,791 discloses a device for stabilization of the lumbar spinal column which requires cutting helical thread marks into the vertebrae that are to be repositioned and then installing an implant to maintain the position. The repositioning device does not stay in the body after the surgery but instead an implant must be inserted to maintain the repositioning.

Therefore, there is a need in the art to combine an implant with a repositioning device in order to reduce the possible repositioning of the vertebrae. There is a further need in the art to provide for adjustment of the vertebrae after an implant has been installed.

SUMMARY OF INVENTION

Disclosed is an apparatus and method for aligning vertebrae due to slippage of the vertebrae relative to each other. To this end, a method and apparatus is disclosed for placing a novel implant between two vertebrae which will move the vertebrae into proper alignment and maintain that alignment until ossification can occur. The implant disclosed is left in situ once the vertebrae have been repositioned. The implant disclosed also provides support for the effected vertebrae superior to that of previous methods known in the prior art. The implant also allows for fine adjustments and post implantation adjustments of the vertebrae superior to that of the prior art.

The disclosed method includes approaching the vertebra anteriorly and removing a portion of vertebral disk between the misaligned vertebrae. Known interbody spacers are then inserted between the vertebrae until the proper restorative height is achieved. The spacers are removed and a distractor is placed between the vertebrae in order to guide the subsequent placement of the implant. A novel gate is inserted over a novel distractor to properly guide a novel saw mechanism to cut into the vertebrae at precise locations and allow for the insertion of a novel implant. Different gates are provided depending on the necessary restorative height to be achieved and amount of slip between the vertebrae.

The disclosed implant has two halves which include a dovetail groove system which locks the two halves together but allows them to slide with respect to each other along their longitudinal axis. The implant has radial anchors which extend from each half and which fit into slots in the vertebrae cut by the saw. The implant includes a drive bolt which engages the two halves and which, when turned, slides one half of the implant in relation to the other. The advancing halves of the implant carry the radial anchors with them that align the vertebrae. Depending on the amount of slip between the vertebrae and the necessary restorative height, different sized implants and associated tools may be used.

The implant is inserted through a distractor by use of an inserter. The halves of the implant are aligned so that the radial anchors correspond to slots made in the misaligned vertebrae. The implant is rotated into place by the inserter such that the radial anchors fit securely in the slots previously made by the saw in the vertebrae. The distractor is then removed.

In the case of anterior listhesis of the superior vertebra, the drive bolt of the implant is then rotated so that the upper half of the implant is advanced posteriorly. The superior vertebra is pulled posteriorly with respect to the inferior vertebra by the movement of the upper half of the implant with respect to the lower half.

The position of the implant is locked into place by use of an articulating combination of a nut and a plate, thereby maintaining alignment of the vertebrae. The nut and plate can be removed, allowing for post-surgical adjustment of the implant.

BRIEF DESCRIPTION OF DRAWINGS

The disclosed inventions will be described with reference to the accompanying drawings, which show important sample embodiments of the invention and which are incorporated in the specification hereof by reference, wherein:

FIG. 1 is a side view of a section of human spine characterized by a spondylolisthesis condition.

FIG. 2 is an isometric view of a distractor of a preferred embodiment of the invention.

DETAILED DESCRIPTION OF PREFERRED EMBODIMENTS

Figure 3A:
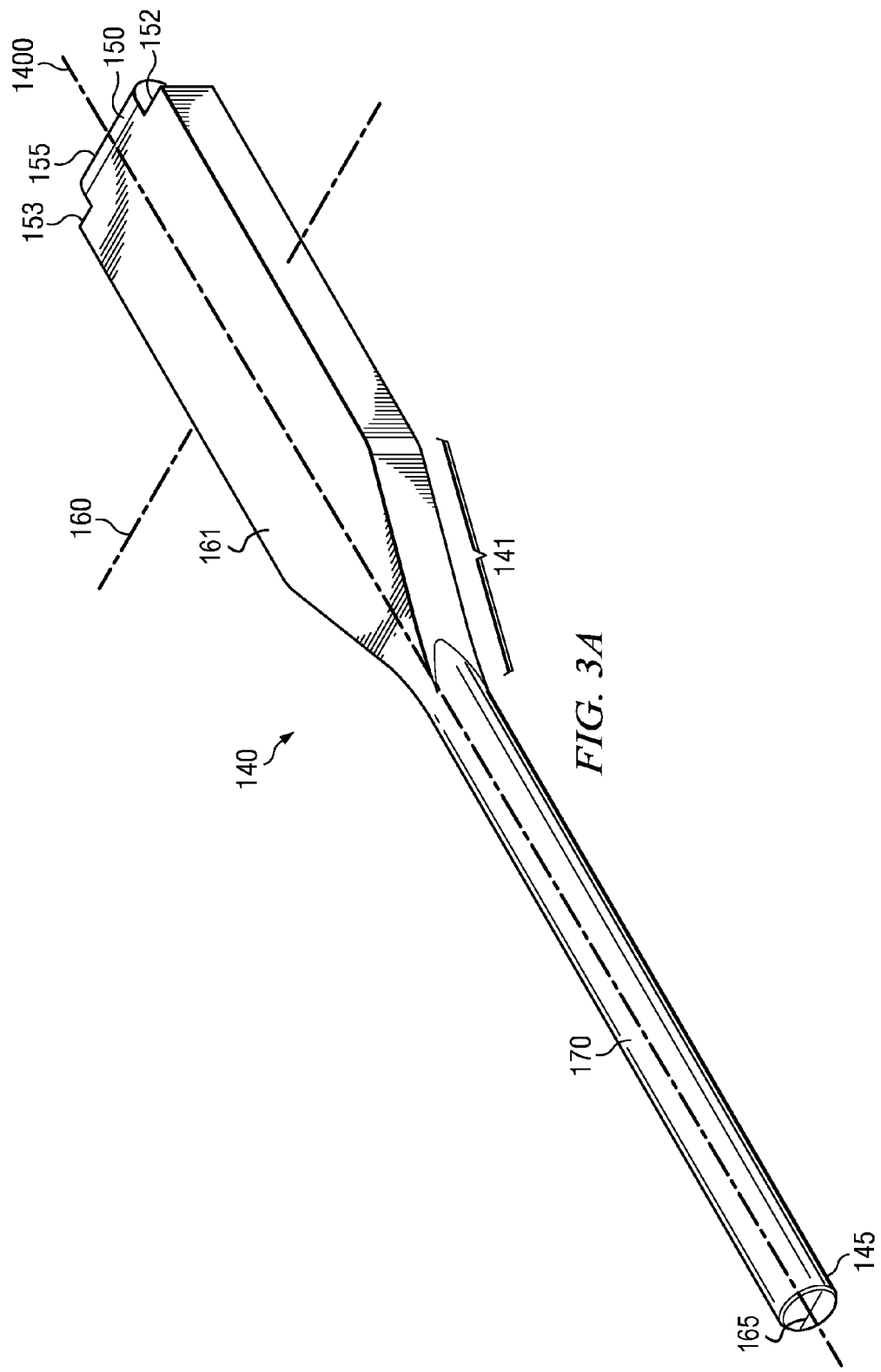
FIG. 3a is an isometric view of an impactor of a preferred embodiment of the invention.

FIG. 1 is an illustration of a lumbar spine in a patient who has contracted spondylolisthesis. The vertebrae 10 are separated by vertebral disk 50. As a result of advanced spondylolisthesis, superior vertebra 20 slips forward in relation to the next inferior vertebra 40 and causes distended disk 70. To repair slippage of the vertebrae, superior vertebra 20 and inferior vertebra 40 are realigned and fused together. To accomplish this, a portion of distended disk 70 is removed and replaced with an implant which maintains realignment and supports the spine until ossification occurs whereby superior vertebra 20 and inferior vertebra 40 are permanently fused.

In order to assure proper alignment, a magnetic resonance image ("MRI") or plain lateral radiographs are used to observe the supine position to measure the severity of the spondylolisthesis condition prior to surgery. The restorative height of the interbody space after partial removal of distended disk 70 and the necessary amount of re-alignment can be estimated by review of the MRI or plain lateral radiographs. The implant size can be determined by the estimates.

The present invention uses the anterior surgical approach to the lumbar spine in order to reach the vertebrae that will receive the implant. The anterior surgical approach to the lumbar spine is understood in the art and is not discussed in detail here.

Referring still to FIG. 1, once the lumbar spine is exposed to the surgeon, superior vertebra 20, inferior vertebra 40, and distended disk 70 are located and identified. A standard marking pin known in the art is inserted into distended disk 70 at the putative midline and left in place.

The implant should be optimally placed at the midline in the sagital plane. Lateral radiographs or x-rays are utilized to confirm the appropriate surgical level and anterior-posterior x-ray imaging demonstrates the midline relative to the marking pin. Once confirmed, the midline of distended disk 70 is marked on distended disk 70 by use of generally accepted marking means. The marking pin is then removed.

Portion of distended disk 70 is removed. Boundaries of generous rectangular annulatomy are created in distended disk 70 by use of scalpel. The size of the annulatomy will depend upon the size of the implant and allows additional space on either side of implant to allow interbody arthodesis on both sides of implant after implant is deployed. The width of annulatomy will be in the range of between about 2 cm and about 5 cm. Portion of distended disk 70 within the boundary of annulatomy is removed by use of rongeurs and curettes.

Vertebral endplate preparation is performed in standard fashion as known in the art while maintaining cortical endplate integrity centrally. Anterior osteophytes may also be removed from the ventral aspect of the vertebral bodies during this stage of the surgery.

In order to gain the appropriate restorative height between superior vertebra 20 and inferior vertebra 40, sequentially larger interbody spreaders are impacted into the rectangular annulotomy in distended disk 70 until optimal height restoration is achieved. Interbody spreaders are known in the art. When optimal height restoration is achieved, interbody spreaders are removed and appropriate height distractor 110 is inserted.

FIG. 2 illustrates one embodiment of distractor 110. Distractor 110 is made of titanium, stainless steel, or other commercially available material which is easily sterilized. Rigid plastics can be used such as polyvinyl chloride (PVC) in disposable embodiments. Distractor 110 is rectangular in cross-section and includes hollow distractor channel 115. Distractor channel 115 is rectangular in cross-section and runs the length of distractor 110 along distractor body longitudinal axis 1100. The dimensions of distractor 110 vary depending on the optimal height restoration to be achieved, but height of distractor 110 should generally range between about 0.5 cm and about 1.5 cm and the width of distractor 110 should range between about 2 cm and about 5 cm. The length of distractor 110 is between about 30 cm and about 60 cm. The thickness of walls of distractor 110 should range between about 1 mm and about 5 mm depending on the material of construction to achieve a rigid structure. The dimensions of distractor channel 115 should range between about 0.4 cm and about 1.4 cm high, about 1.9 cm and about 4.9 cm wide.

Posterior end of distractor 110 contains distractor arm 117 and distractor arm 118. Distractor arm 117 extends longitudinally from side 80 of distractor 110. Distractor arm 117 includes distractor point guide 246 having angled surfaces 253 and 254. Opposing angled surfaces 253 and 254 is distractor stop 119. Distractor arm 118 extends longitudinally from the side 81 of distractor 110 and includes distractor point guide 256 having rounded surfaces 258 and 255. Opposing rounded surfaces 258 and 255 is distractor stop 122. The height of distractor arm 117 and distractor arm 118 are approximately the same as the height of distractor 110. The width of distractor arm 117 and distractor arm 118 are between about 0.5 mm and about 1 mm. The width of the distractor arms should provide rigidity with respect to the body of the distractor. Distractor arm 118 and distractor arm 117 form implant hollow 130. End gap 120 is formed at the forward end of implant hollow 130. The preferred design of end gap 120 is between about 1.7 cm and about 4.7 cm. Distractor stop 122 and distractor stop 119 are between about 0.5 mm and about 2 mm in length.

Torque handle 235 is rigidly mounted to distractor body 99. Torque handle 235 is generally in the range of about 2 cm to about 5 cm in length with a diameter in the range of about 0.5 cm to about 2 cm. The preferred location of torque handle 235 is approximately between ¼ to ½ from the anterior end 111 of distractor 110. A set of distractor graticules 135 are etched at 1 mm intervals on the side of distractor 110 along the outside of distractor arm 118 and distractor arm 117.

In the preferred embodiment, the cross-sectional height and width of distractor 110 may vary. In its preferred use, a set of variable height distractors is provided so that the distractor height which matches the vertical distance between the vertebrae may be used during surgery. The preferred set of heights preferably varies in one millimeter increments between about 5 mm and about 2 cm.

FIG. 3a illustrates the preferred embodiment of impactor 140. Impactor 140 includes impactor handle 170 which is cylindrical with a diameter in the range of about 0.3 cm and about 2 cm and is centered along the impactor longitudinal axis 1400. The length of impactor handle 170 ranges between about 5 cm and about 25 cm. In one embodiment, impactor handle 170 is etched with impactor centerline 165 across its diameter. Impactor centerline 165 is parallel to the latitudinal axis 160 of impactor 140.

Impactor body 161 is formed integrally with impactor handle 170. Impactor body 161 is rectangular in cross-section and sized to fit within distractor channel 115 without excessive play. In the preferred embodiment, the impactor body is sized to allow for approximately 0.3 mm play between the exterior of the impactor body and the distractor channel.

Angled section 141 extends from impactor handle 170 to impactor body 161 at an angle between about 25 and about 65 degrees. Angled section 141 serves to center the impactor handle with respect to the impactor body and distribute impact loads from the impactor handle to the impactor body as will be further described. The preferred length of impactor body 161 should range between about 30 cm and about 45 cm. The posterior end of impactor body 161 includes impactor seat 150 integrally formed with impactor body 161. Impactor seat 150 is sized and shaped to fit within end gap 120 shown in FIG. 2. Impactor seat 150 has rounded surface 155. On either side of impactor seat 150 are stop surface 152 and stop surface 153. Impactor 140 is preferably made from titanium, stainless steel, or other materials which are readily sterilized or from a rigid plastic such as PVC which may be disposed of after use.

Other cross-sectional shapes of the impactor and distractor are also acceptable, such as elliptical, as long as the impactor fits inside the distractor channel such that it can move longitudinally in distractor channel 115 without rotation and without significant "play" or angular displacement.

Figure 3B:
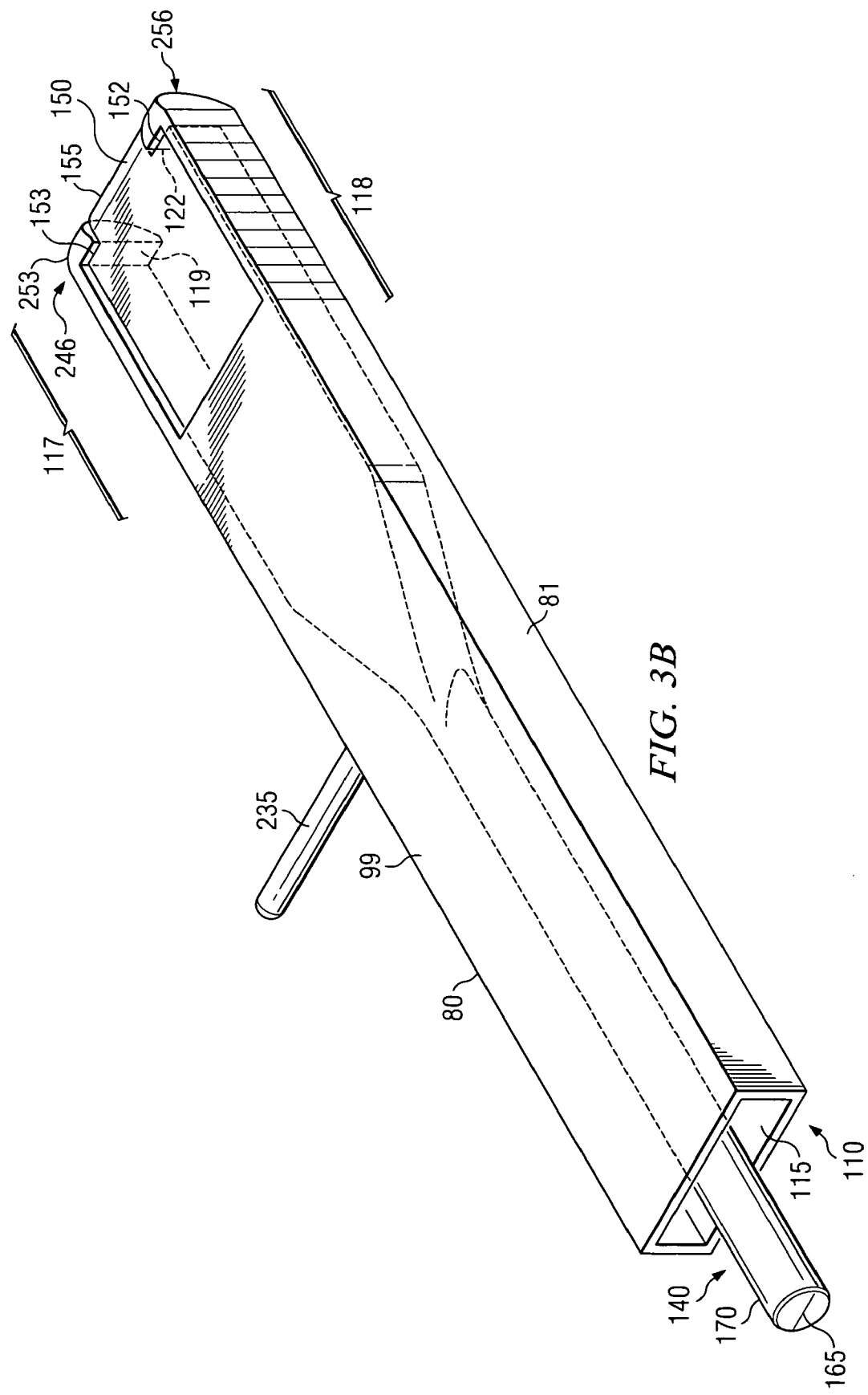
FIG. 3b is an isometric view of an impactor in conjunction with a distractor of a preferred embodiment of the invention.

In use, impactor 140 is placed inside distractor channel 115, such that impactor seat 150 fits into end gap 120 as shown in FIG. 3b. Impactor centerline 165 is aligned with the anatomical midline marked previously. Distractor 110 and impactor 140 are aligned with the anatomical midline and inserted into the rectangular annulatomy in distended disk 70. A mallet is used to tap impactor 140 at striking end 145 and move distractor 110 into the midline sagital plane under fluoroscopic guidance until posterior edge of distractor 110 reaches the dorsal epiphyseal ring on the ventrally superior vertebra 20. Impactor 140 is then withdrawn from distractor channel 115 and distractor 110 is left in situ.

In the preferred embodiment, impactor 140 is also provided in a set of variable sizes to match the set of variable sizes of distractor 110, as previously described.

Figure 4:
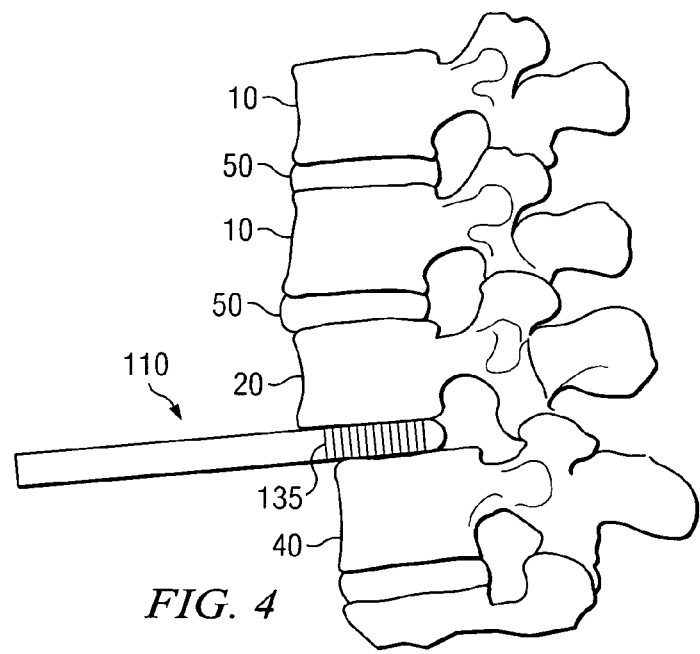
FIG. 4 is a side view of a section of a human spine with the distractor in place between vertebrae.

FIG. 4 shows distractor 110 in situ between superior vertebra 20 and inferior vertebra 40. Distractor 110 is between superior vertebra 20 and inferior vertebra 40. Once in position, distractor graticules 135 are used to gauge the amount of slip existing between superior vertebra 20 and inferior vertebra 40.

Figure 5A:
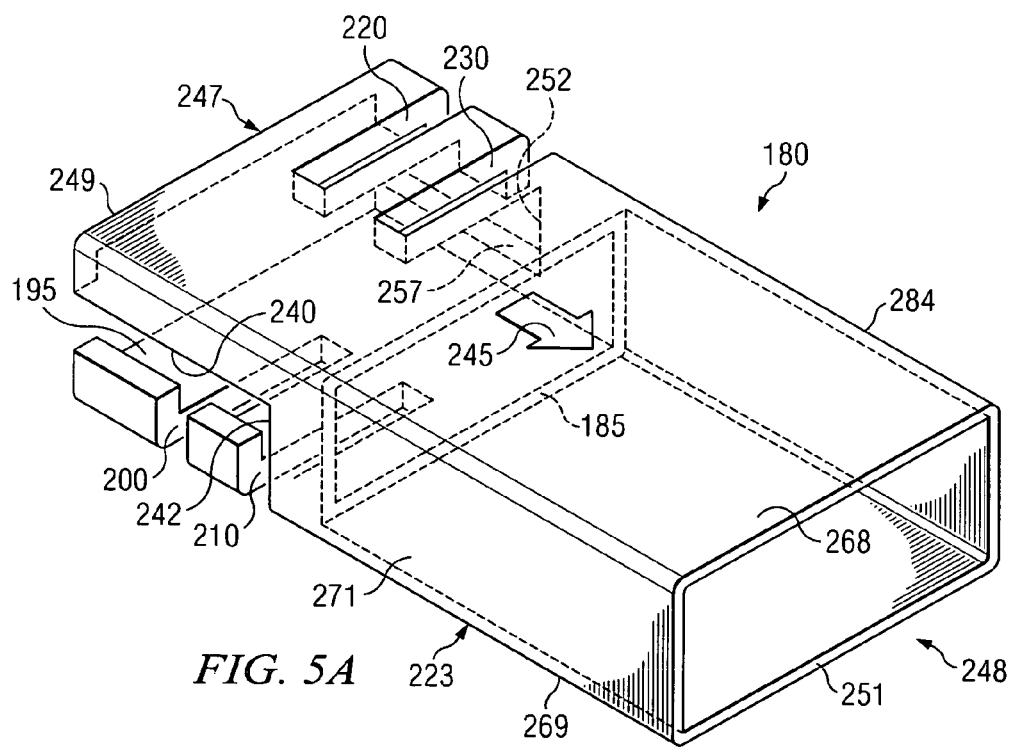
FIG. 5a is a partial isometric view of a gate of a preferred embodiment of the invention.
Figure 5B:
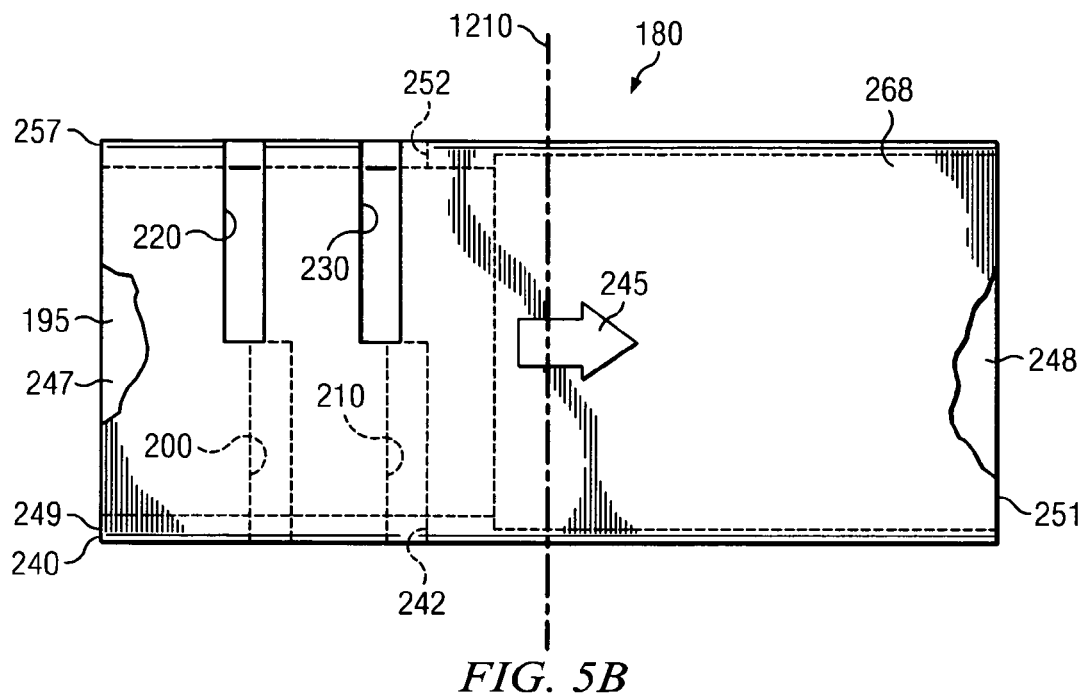
FIG. 5b is a plan view of a gate of a preferred embodiment of the invention.
Figure 5C:
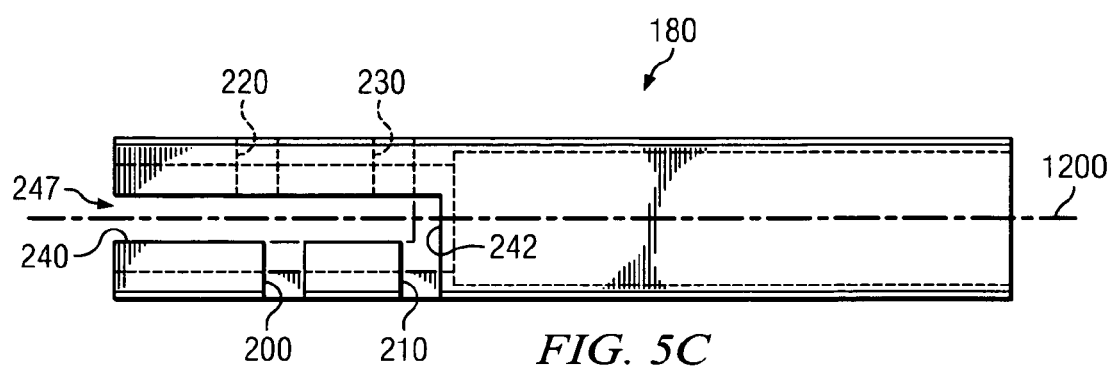
FIG. 5c is an elevated view of a gate of a preferred embodiment of the invention.

FIGS. 5a, 5b and 5c illustrate an embodiment of gate 180. Gate 180 has a gate body 223 bordered by side wall 271, bottom side 269, side wall 284 and top side 268. The gate body extending along gate longitudinal axis 1200 also includes saw end 249 and distractor end 251. In the preferred embodiment, gate 180 has a length of between about 5 cm and about 10 cm along gate longitudinal axis 1200, a width of between about 2.2 cm and 5.8 cm along gate latitudinal axis 1210 and a height of between about 0.7 cm and about 2.9 cm.

Gate 180 is provided with saw guide 220 and saw guide 230. Saw guides 220 and 230 are a pair of slots which are situated approximately the center of top side 268 to the center of side wall 284, encompassing approximately ¼ of the perimeter of gate body 223. The pair of saw guides are in parallel planes. Saw guide 220 and saw guide 230 terminate in handle guide 257. Handle guide 257 forms a slot generally in the center of side wall 284. Handle guide 257 is provided with handle stop 252. The width of saw guides 220 and 230 and handle guide 257 in the preferred embodiment is between about 0.5 cm and 1.5 cm.

Gate body 223 is also provided with saw guide 200 and saw guide 210. Saw guides 200 and 210 are a matched pair of slots which are situated approximately the center of bottom side 269 to the center of side wall 271, encompassing approximately ¼ of the perimeter of gate body 223. The pair of saw guides are in parallel planes. Saw guide 200 and saw guide 210 terminate in handle guide 240. Handle guide 240 forms a slot generally in the center of side wall 271. Handle guide 240 is provided with handle stop 242. The width of saw guide 200, saw guide 210 and handle guide 240 in preferred embodiment is between about 0.5 cm and about 1.5 cm.

Saw guide 220, saw guide 230 and handle guide 257 are ductedly connected. Saw guide 220 and saw guide 230 are on centers of between about 0.5 cm to 3.5 cm in the preferred embodiment. Further, saw guide 220 is approximately 0.9 cm from saw end 249.

Saw guide 210, saw guide 200 and handle guide 240 are ductedly connected. Saw guide 210 and saw guide 200 are on centers of between about 0.5 cm to 3.5 cm in the preferred embodiment. Further, saw guide 210 is approximately 1.9 cm from saw end 249.

Figure 6:
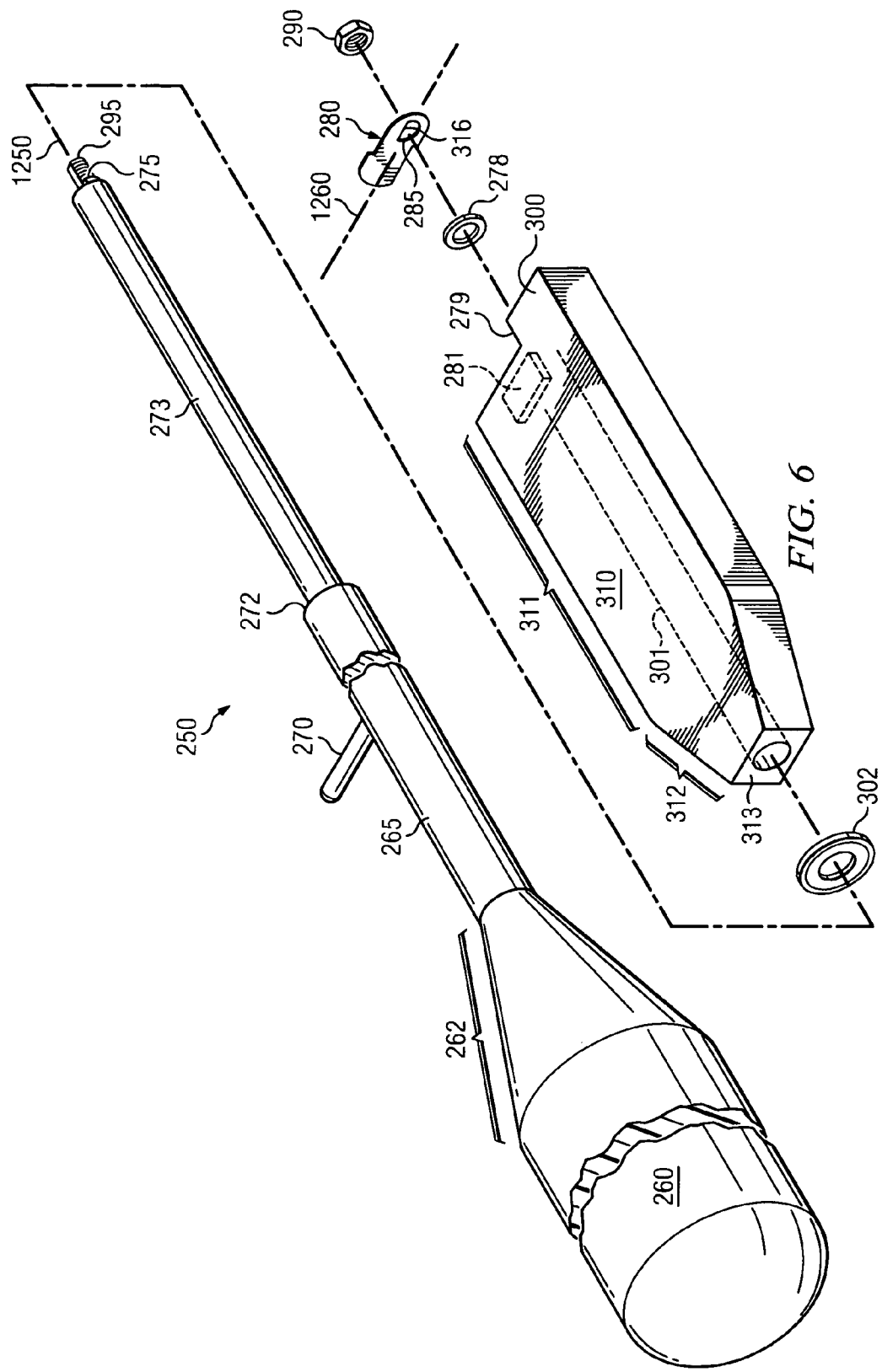
FIG. 6 is an exploded isometric view of a saw of a preferred embodiment of the invention.
Figure 7A:
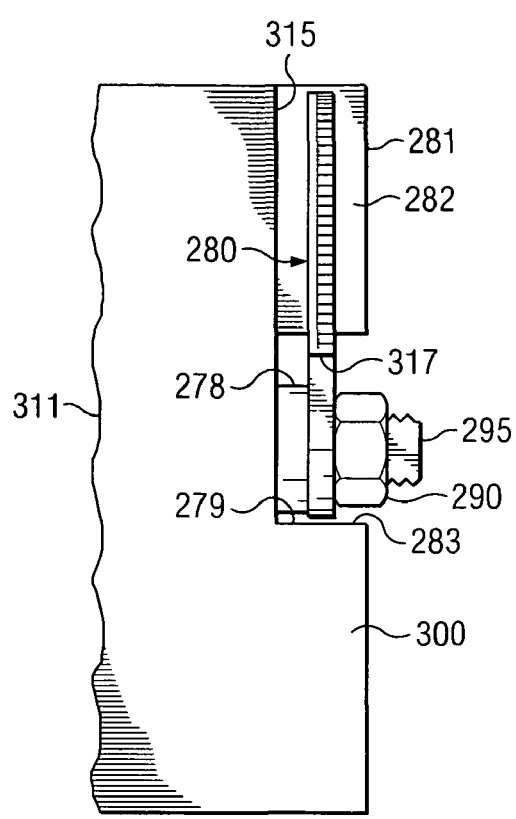
FIG. 7a is a partial plan view of the relational section of the saw of a preferred embodiment of the invention.
Figure 7B:
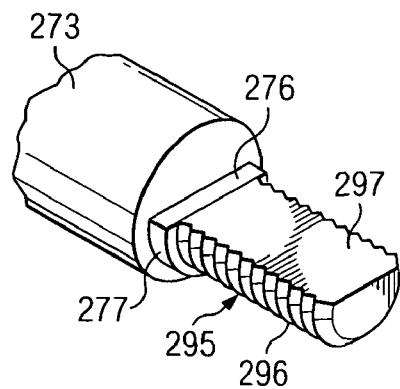
FIG. 7b is a partial isometric view of the spindle shaft of a preferred embodiment of the invention.
Figure 7C:
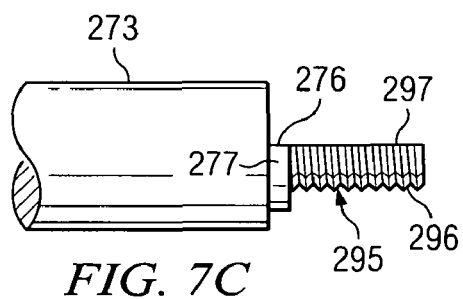
FIG. 7c is a partial side view of the spindle shaft of a preferred embodiment of the invention.

Gate body 223 is further provided with interior channel 195 which is longitudinally centered within gate body 223. Interior channel 195 includes saw entrance 247. Saw entrance 247 in the preferred embodiment has dimensions slightly larger than guide body 310 which will be described in more detail with respect to FIG. 6. The diameter of saw entrance 247 is maintained by interior channel 195 from saw entrance 247 until gate lip 185. At gate lip 185, interior channel 195 increases in height and width to accommodate the exterior of distractor 110. The dimensions of interior channel 195 remain constant from gate lip 185 to distractor end 251 terminating in distractor entrance 248.

In one embodiment, gate 180 can also include raised indicator arrow 245 or other visual aid or tactile indicator to indicate which end of gate 180 is to be inserted over distractor 110.

In the preferred embodiment, many gates are provided in a kit during surgery. The gates each have saw guides that are spaced apart at different lengths with respect to the top and the bottom of each gate. The different spacings correspond to different distances that the vertebrae have slipped. In one preferred embodiment, in the less severe cases, saw guides 230 and 220 will be offset from saw guides 200 and 210 by about 1 mm. The offset between saw guides 230 and 220 and saw guides 200 and 210 will increase by 2 mm increments. In more severe cases, the amount of slip will be more pronounced and the offset can be approximately 20 mm. Position of saw guides 200 and 210 on gate 180 will stay constant. The gates also vary in height to match the variable height of the distractor.

Referring now to FIGS. 6 and 7A, 7B and 7C, an embodiment of saw 250 can be seen. Saw 250 includes saw handle 260 to conical section 262. Conical section 262 is connected to handle post 265. Handle post 265 integrally supports saw guide post 270. Saw guide post 270 is perpendicular to the longitudinal axis 1250 of saw 250. Handle post 265 includes abutment surface 272 narrows to the diameter of spindle shaft 273. Abutment surface 272 connects spindle shaft 273 with blade seating shoulder 275. Blade seating shoulder 275 is flat surface 276 and semicircular section 277. Blade seating shoulder 275 is connected to bolt 295. Bolt 295 has threaded section 296 which is directly adjacent to flat surface 276 and semicircular section 277. Bolt 295 has a threaded section 296 and a flat surface 297.

Saw 250 includes guide body 310. Guide body 310 includes a rectangular section 311 and an angular section 312. Rectangular section 311 in the preferred embodiment is sized to fit within saw entrance 247 as shown in FIG. 5b and distractor channel 115 shown in FIG. 2. The rectangular section tolerance must be such that rectangular section 311 slides longitudinally with respect to distractor channel 115 and interior channel 195 without significant angular play about the longitudinal axis. In the preferred embodiment, these tolerances are approximately 0.3 mm. Angular section 312 connects to flat surface 313. Guide body 310 also includes spindle hole 301 which traverses the longitudinal axis of guide body 310 and is sized to fit around spindle shaft 273. Spindle hole 301 is sized to allow rotation with respect to spindle shaft 273.

Rectangular section 311 includes spacer 300, saw alignment stop 281 and saw alignment stop 279. As can be seen best in FIG. 7a and FIG. 6, saw alignment stop 281 includes a horizontal surface 282. Saw alignment stop 279 includes vertical surface 283.

When assembled, saw 250 provides for 90 degrees rotation of saw handle 260 with respect to guide body 310. Thrust bearing 302 rests adjacent abutment surface 272. Guide body 310 rests on spindle shaft 273 via spindle hole 301. Flat surface 313 is adjacent angular section 312 and thrust bearing 302 providing a bearing surface between abutment surface 272 and flat surface 313. Thrust bearing 278 resides around semicircular section 277 of blade seating shoulder 275 adjacent vertical end 315 of rectangular section 311. Locking hole 285 of saw blade 280 is adjacent flat surface 276 and semicircular section 277 of blade seating shoulder 275. Locking hole 285 includes flat surface 316 which when brought into contact with flat surface 276, prevents rotation of saw blade 280 with respect to blade seating shoulder 275, consequently, with respect to saw handle 260. Lock nut 290 is threaded onto threaded section 296 of bolt 295. Flat surface 276, flat surface 316 and saw alignment stop 281 are parallel with the axis of saw guide post 270. In one embodiment, saw blade longitudinal axis 1260 of saw blade 280 is also parallel with the axis of saw guide post 270.

Saw 250 and all its components are made from titanium, stainless steel, or other material which is used with surgical tools and equipment. In the preferred embodiment, rectangular section 311 of saw 250 is provided in several sizes in a set of several sizes to match the sizes of the distractor 110, as previously described. Alternatively, a set of several saws 250 is provided, each having a rectangular section 311 whose cross-section is sized to match the distractor channel 115 of the set of distractors 110. In addition, a set of blades may be provided each having different dimensions to achieve different lumbar dimensions.

Figure 8A:
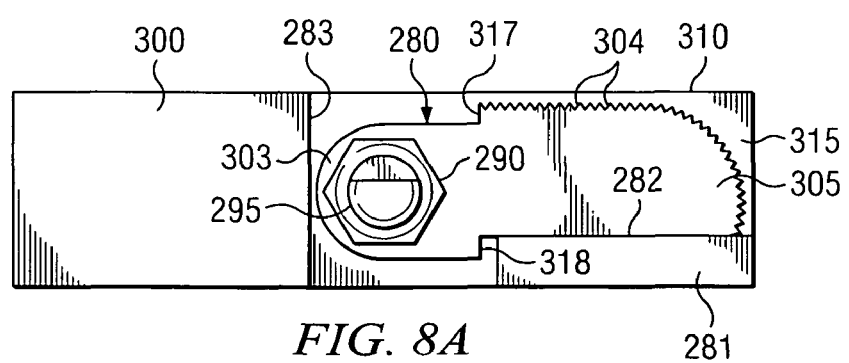
FIG. 8a is an end view of the saw with the saw blade in a lowered position of a preferred embodiment of the invention.
Figure 8B:
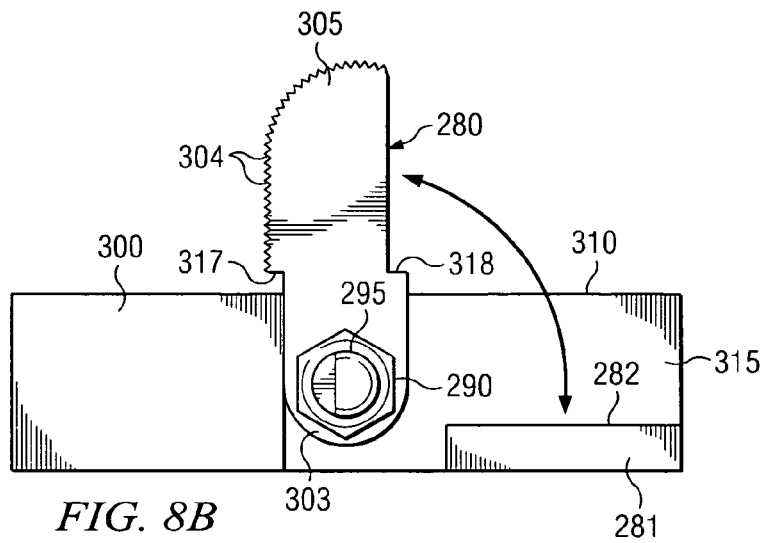
FIG. 8b is an end view of the saw with the saw blade in a raised position of a preferred embodiment of the invention.

FIGS. 8a and 8b are end views of saw 250. FIG. 8a illustrates saw blade 280 in lowered position. In lowered position, saw blade 280 is flush with guide body 310. FIG. 8b illustrates saw blade 280 in raised position. In raised position, saw blade 280 is perpendicular to guide body 310.

In the preferred embodiment, saw blade 280 is between 0.9 cm and 4.9 cm long with a width of between 1 mm and 5 mm. Saw blade 280 has a flat bottom and two curved ends 303 and 305. Saw blade 280 includes a locking hole 285 of approximate diameter and shape as bolt 295. Curved end 305 includes saw teeth 304 having a height of about 0.5 mm and about 1.5 mm. Saw blade 280 also includes notches 317 and 318. As shown in FIG. 8b, saw blade 280 in its raised position rests adjacent vertical surface 283 which prevents it from rotating counterclockwise. In lowered position, as shown in FIG. 8*a*, notch 318 rests adjacent horizontal surface 282 and prevents rotation of the saw blade clockwise.

Figure 9:
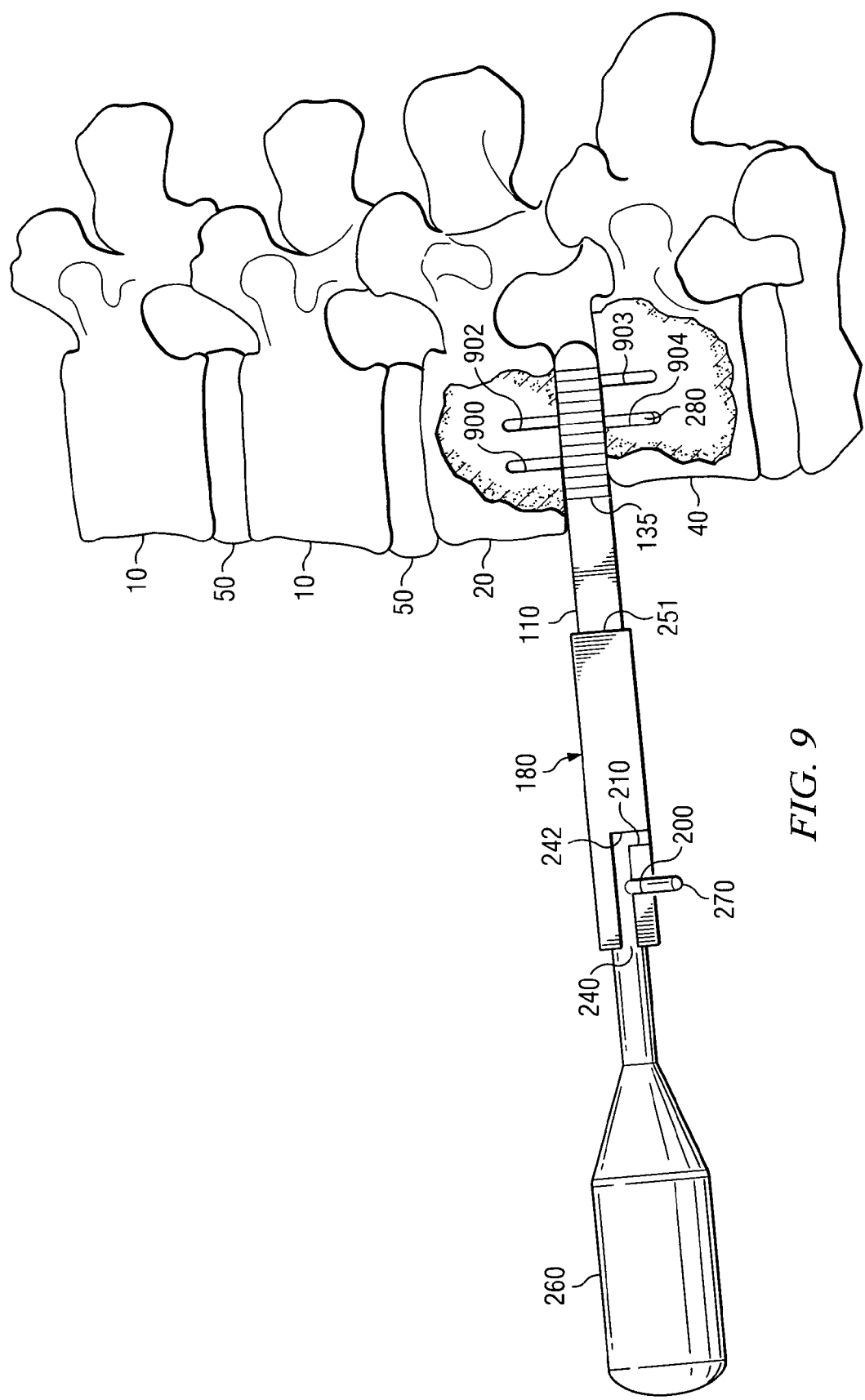
FIG. 9 is a cut away side view of section of a human spine with the distractor, gate, and saw in place between the vertebrae.

Referring now to FIG. 9, in use, gate 180 is placed over the anterior end of distractor 110 and advanced until anterior end 111 rests against gate lip 185. Saw 250 is placed in lowered position. Rectangular section 311 is placed in interior channel 195 and advanced through distractor channel 115 until spacer 300 reaches distractor stop 122 or saw guide post 270 reaches handle stop 242.

In use, the saw is used to make two sets of receiving notches in the upper and lower vertebrae that correspond to the positions of the saw guides. More particularly, saw 250 is retracted until saw guide post 270 is directly adjacent saw guide 230. Saw handle 260 is rotated clockwise 90 degrees such that saw guide post 270 advances through saw guide 230 on gate 180. Rotation of saw handle 260 will rotate saw blade 280 causing it to cut into superior vertebra 20 thereby forming a slot 900. Distractor torque handle 235 is grasped to apply counter torque and prevent rotation of the saw from displacing distractor 110 angularly with respect to the effected vertebrae. Saw handle 260 is then rotated counterclockwise positioning saw guide post 270 in handle guide 257. Saw 250 is then extracted such that saw guide post 270 is adjacent saw guide 220. Saw handle 260 is then rotated clockwise 90 degrees such that saw guide post 270 advances into saw guide 220. Rotation of saw handle 260 rotates saw blade 280 thereby cutting into superior vertebra 20 and forming slot 902. Saw guide post 270 is then rotated counter-clockwise so that saw guide post 270 resides in handle guide 257.

Saw blade 280 is placed in its lowered position. Saw 250 is then removed from distractor channel 115 through interior channel 195. Saw 250 is then rotated 180 degrees about its axis and rectangular section 311 replaced is in interior channel 195 of gate 180. Saw 250 is further reinserted into distractor channel 115.

Saw guide post 270 is adjacent saw guide 210. The saw handle is rotated clockwise 90 degrees such that saw guide post 270 enters saw guide 210. Rotation of saw handle 260 consequently rotates saw blade 280 exposing saw teeth 304 to inferior vertebra 40 thereby cutting into inferior vertebrae 40 thereby forming slot 903. Distractor torque handle 235 is used to apply counter torque and prevent the saw rotation from displacing distractor 110. Saw handle 260 is then rotated clockwise such that saw guide post 270 advances through the saw guide and into handle guide 240. Saw 250 is then extracted such that saw guide post 270 advances through handle guide 240 until it is adjacent saw guide 200. Saw handle 260 is then rotated 90 degrees such that saw guide post 270 advances into saw guide 200. The rotation of saw handle 260 rotates saw blade 280 causing a second cut into inferior vertebra 40 thereby forming slot 904.

Saw 250 is removed through distractor channel 115 and interior channel 195. Gate 180 is then removed from the anterior end of distractor 110.

Slots 900, 902, 903 and 904 in superior vertebra 20 and inferior vertebra 40 are substantially consistent with the spacing on gate 180 between saw guides 200, 210, 220, and 230, respectively.

The novel implant is then prepared to be inserted.

Figure 11:
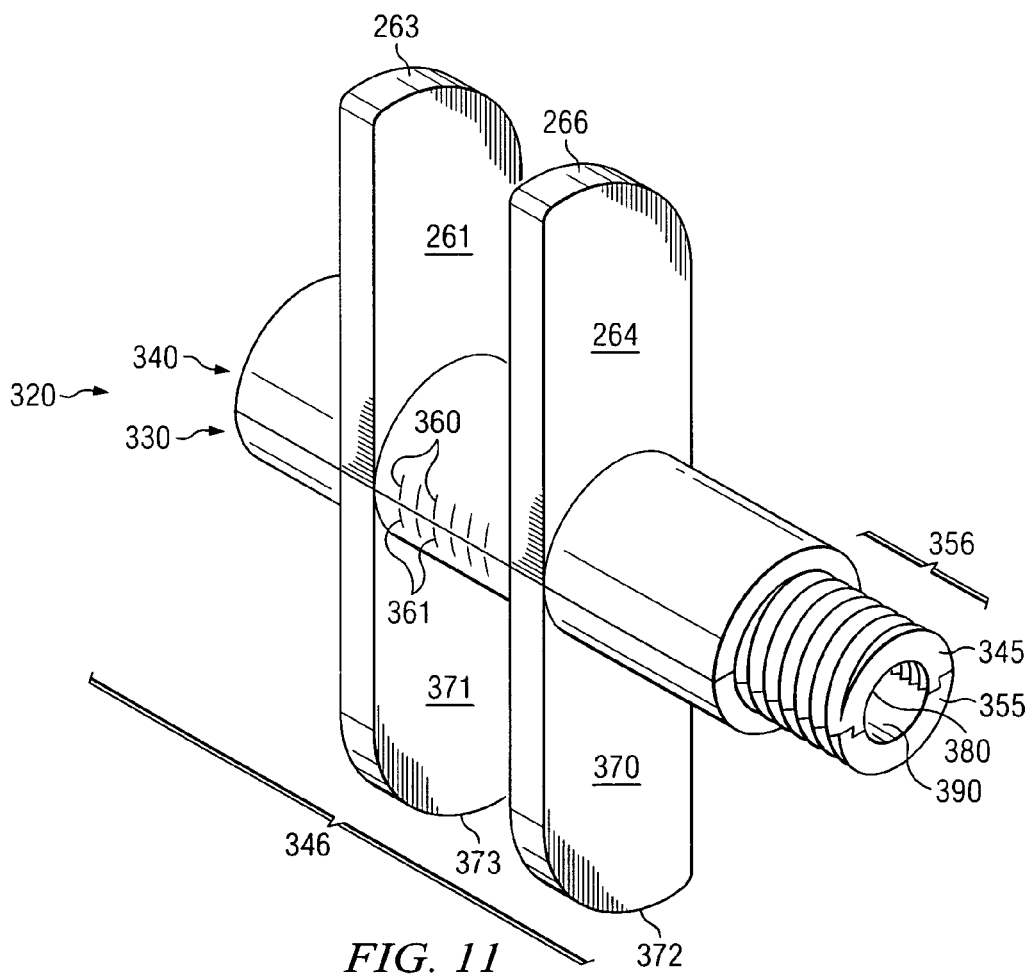
FIG. 11 is an isometric view of the implant of a preferred embodiment of the invention.
Figure 10:
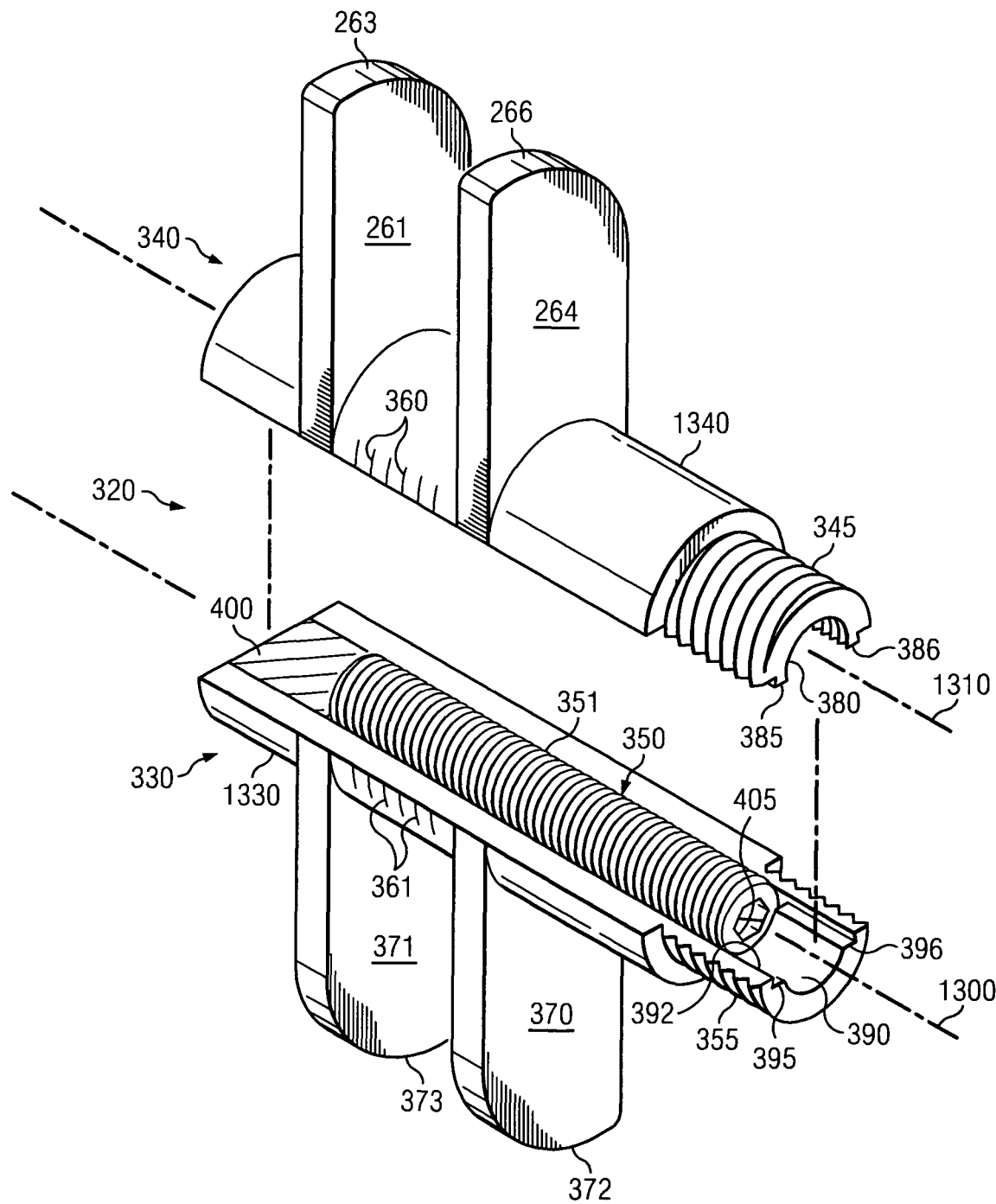
FIG. 10 is an exploded isometric view of the implant of a preferred embodiment of the invention.
Figure 12:
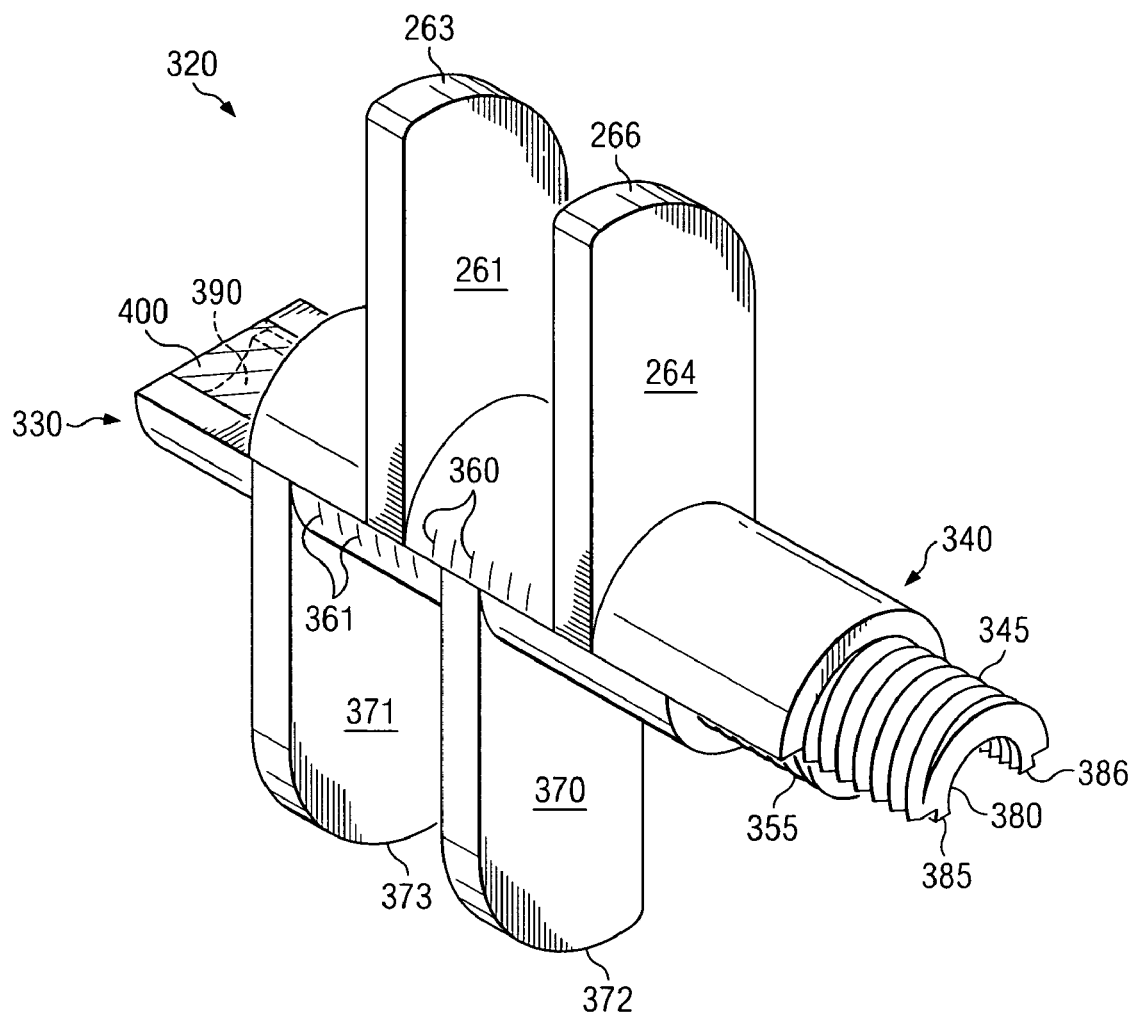
FIG. 12 is an isometric view of the implant in an extended position of a preferred embodiment of the invention.

Referring to FIGS. 10, 11 and 12, implant 320 is described. Implant 320 is comprised of two semi-cylindrical halves, upper half 340 and lower half 330. Upper half 340 extends along an upper half longitudinal axis 1310 and includes parallel radially exposed and planar radial anchors 264 and 261 extending perpendicularly from an upper half outer surface 1340. The radial anchors are integrally formed with upper half 340. Radial anchor 264 further includes curved surface 266. Radial anchor 261 includes curved surface 263.

Lower half 330 extends along a lower half longitudinal axis 1300 and includes two parallel planar radial anchors 370 and 371. Radial anchors 370 and 371 are integrally formed with lower half 330 extending perpendicularly from a lower half outer surface 1330. Radial anchor 370 includes curved surface 372. Radial anchor 371 includes curved surface 373.

Upper half 340 includes upper threaded collar 345. Lower half 330 includes lower threaded collar 355. The exterior of the upper half includes index marks 360. Index marks 360 correspond with index marks 361 on lower half 330.

Upper half 340 includes upper channel 380 which is threaded with a set of channel threads. Lower half 330 includes lower channel 390. Lower channel 390 is not threaded. Upper half 340 is joined to lower half 330 with a mating interconnection between dovetail guide 386 and dovetail guide 385 found on upper half 340 and dovetail slot 396 and dovetail slot 395, respectively, located on lower half 330.

Lower half 330 includes set screw stop 400 integrally formed with lower half 330 and residing within lower channel 390. Set screw stop 400 is solid plug which fills lower channel 390 beyond end of set screw 350. Set screw 350 includes spanner slot 405 and a set of set screw threads 351.

Lower half 330 includes set screw step 392. Set screw step 392 extends into upper channel 380 and in upper half 340 and lower channel 390 in lower half 330. Set screw step 392 decreases diameter of upper channel 380 and lower channel 390 by approximately 2 mm.

As can best be seen in FIG. 12, when assembled, upper half 340 and lower half 330 of implant 320 are engaged in a sliding relationship provided by the dovetail guides 385 and 386 residing in dovetail slots 395 and 396. As can be seen in FIG. 11, when assembled, upper half 340 and lower half 330 form implant body 346. Radial anchor 264 is aligned with radial anchor 370. Radial anchor 261 is aligned with radial anchor 371. Furthermore, upper threaded collar 345 and lower threaded collar 355 are aligned and form a cylindrical threaded attachment collar 356.

In use, set screw 350 can be rotated either counter-clockwise or clockwise within lower channel 390 and upper channel 380. The set screw is retained in position by set screw stop 400 and set screw step 392. As set screw 350 is rotated, set of set screw threads 351 engage the set of channel threads on upper channel 380 and slide upper half 340 with respect to lower half 330. As upper half 340 and lower half 330 are displaced, radial anchors 264 and 261 are displaced with respect to radial anchors 370 and 371 along the longitudinal axis of implant 320. The set of channel threads and the set of set screw threads have a pre-determined relationship to allow upper half 340 to move a pre-determined distance in relation to lower half 330 when set screw 350 is rotated a pre-determined angle of rotation.

Implant 320 in the preferred embodiment is made from titanium, stainless steel, alloys such as titanium allow, or other materials which are easily sterilizable. Implant 320 or parts thereof, may also be made from composite materials such as synthetic bone. Some composites or synthetic bone products include demineralized bone matrix, collagen, ceramics, cements, and polymers, such as silicone and some acrylics and include products such as Vitoss, Cortoss, Rhakoss, Pro Osteon, and Gu-Bang.

In the preferred embodiment, implant body 346 is between about 0.5 cm to about 2.5 cm in diameter and between about 2.0 cm and about 4.5 cm in length. In the preferred embodiment, cylindrical threaded attachment collar 356 is between about 0.4 to about 2.4 cm in diameter and between about 0.5 and 2.0 cm in length. In the preferred embodiment, radial anchors 264, 261, 370 and 371 have a height (as measured from the center plane of the implant) of between about 0.5 cm and about 3.5 cm with an aspect ratio of ½ to 1½ between radial anchors 264, 261, 370, and 371 and diameter of implant body 346.

In the preferred embodiment, upper half 340 includes exactly two radial anchors and lower half 330 includes exactly two radial anchors. However, in other embodiments, the upper half and lower half of the implant may include more or less than two radial anchors. Furthermore, the upper half and lower half of implant 320 do not necessarily need to include the same number of radial anchors. In embodiments which include different numbers of radial anchors, it will be understood by those skilled in the art that the same number of saw guides must be included on gate 180 in order to correspond with the number and orientation of the radial anchors.

Figure 13A:
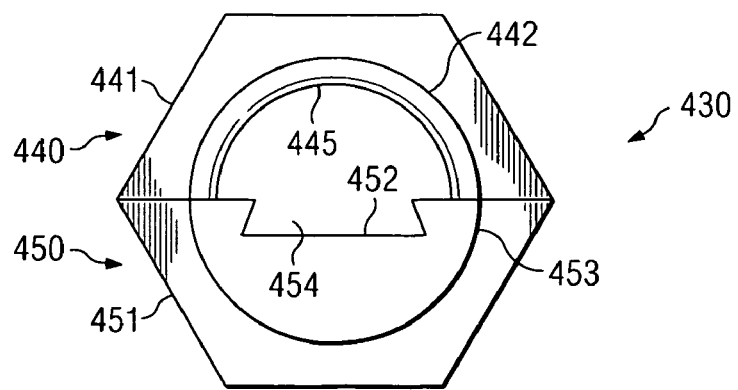
FIG. 13a is an end view of the inserter of a preferred embodiment of the invention.
Figure 13B:
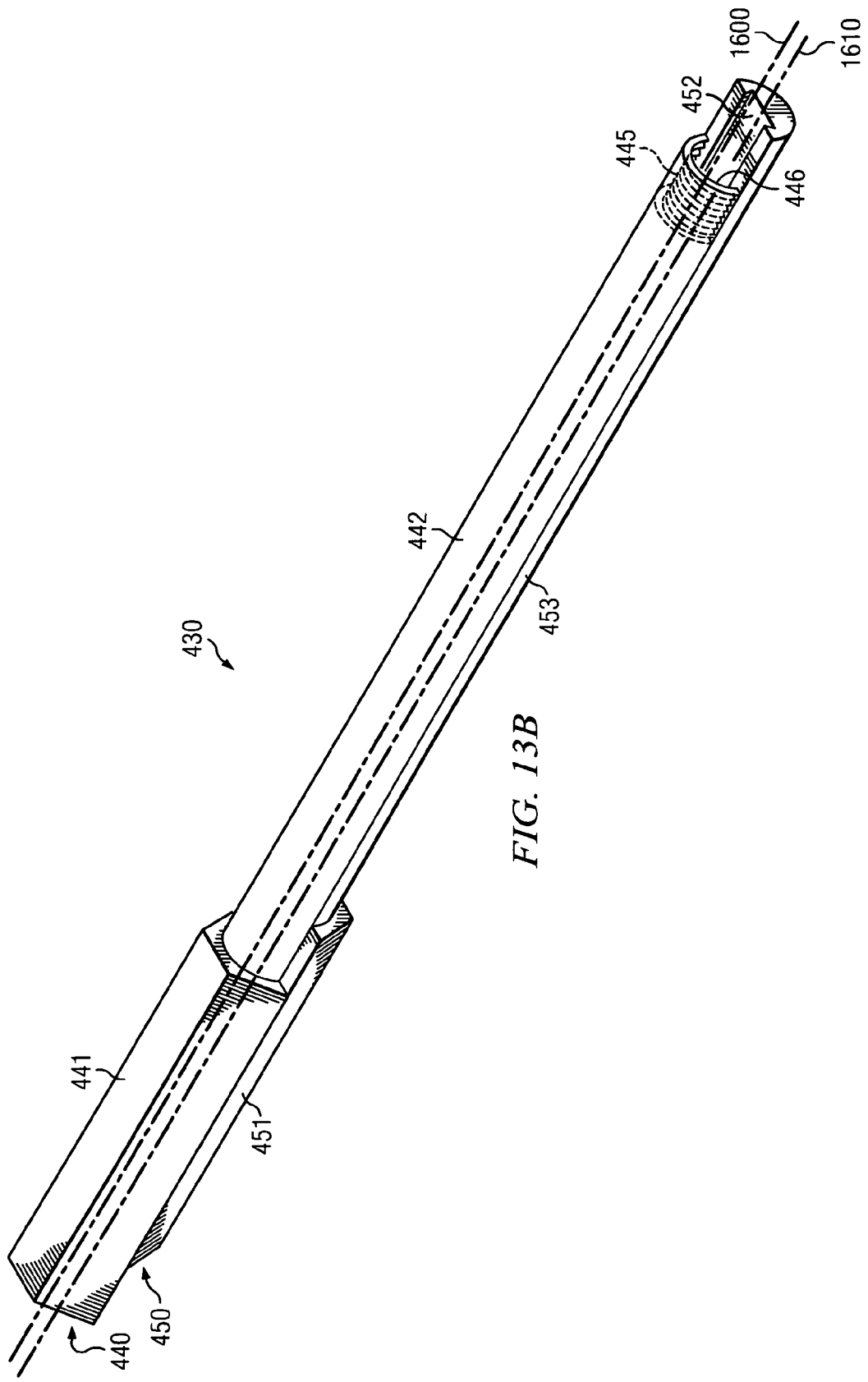
FIG. 13b is an isometric view of the inserter of a preferred embodiment of the invention.

FIGS. 13*a* and 13*b* illustrate inserter 430. Inserter 430 includes upper half 440 and lower half 450. Upper half 440 includes upper hexagonal section 441 and upper cylindrical section 442 having upper longitudinal axis 1600. Within upper cylindrical section 442 resides upper dovetail guide 454. Adjacent upper dovetail guide 454 is implant channel 446. Implant channel 446 includes locking thread 445.

Lower half 450 includes lower hexagonal section 451 and lower cylindrical section 453 having lower longitudinal axis 1610. Lower cylindrical section 453 includes lower dovetail channel 452. Upper dovetail guide 454 fits within lower dovetail channel 452 and allows for sliding movement between upper half 440 and lower half 450. As can best be seen in FIG. 13*b*, when upper half 440 and lower half 450 are assembled, inserter 430 assumes an outer circular perimeter. In the preferred embodiment, this outer circular perimeter is sized to fit within distractor channel 115, shown in FIG. 2, with sufficient clearance to allow for rotation of inserter 430. Further, in the preferred embodiment, the hexagonal shape of upper half 440 and lower half 450 and inserter 430 is sized to allow for rotation with a tool such as a spanner wrench. In the preferred embodiment, the length of inserter 430 is sufficient to span the length of distractor body 99.

Locking thread 445 is sized to mate with upper threaded collar 345 on implant 320 as shown in FIGS. 10, 11 and 12.

Figure 15:
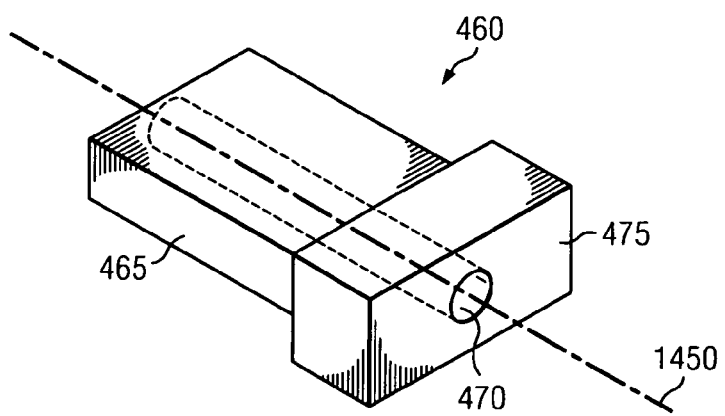
FIG. 15 is an isometric view of a guide block of a preferred embodiment of the invention.

Referring to FIG. 15, guide block 460 will be described. Guide block 460 includes guide block bottom 465 and guide block top 475. Guide block 460 also includes guide hole 470 which is centrally located within the guide block and spans its length along guide block longitudinal axis 1450. Guide block bottom 465 is sized to fit within distractor channel 115. Guide block top 475 is sized so that it will not fit within distractor channel 115 but rather abut anterior end 111 of distractor body 99 (as shown in FIG. 2).

In use, inserter 430 is used to place the implant in position between the affected vertebra and rotated into position. More particularly then to implant the implant, the amount of offset calculated according to the radiograph is reduced to a number of millimeters. The implant is adjusted using upper adjustment index marks 360 and lower adjustment index marks 361 to an offset position using set screw 350. The amount of offset can be observed by observing the offset between index marks 360 and 361. In an alternate embodiment, the offset can be derived by calculating the number of rotations of the set screw and multiplying by the pitch of the threads. In an alternate embodiment, the pitch of the threads is set to a convenient number so that a single rotation of the set screw results in a predetermined movement of the upper and lower halves, such as 1 mm for example. An example of an offset position is shown in FIG. 12.

In use, inserter 430 is assembled and its cylindrical section is guided into and through guide hole 470 until guide block top 475 reaches the hexagonal section of the inserter.

Figure 14:
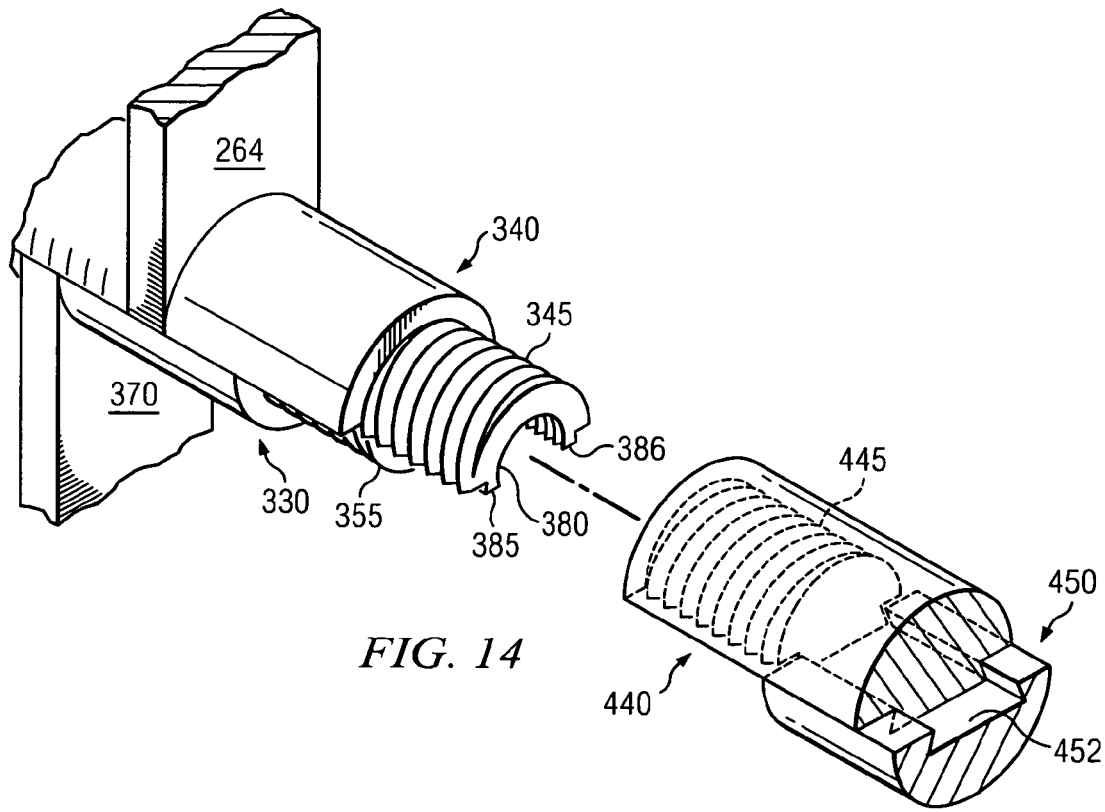
FIG. 14 is a partial isometric view of the inserter and the implant of a preferred embodiment of the invention prior to attachment.

Implant 320 is then connected to inserter 430 as shown in FIG. 14. Locking thread 445 of inserter 430 is engaged with upper threaded collar 345 of implant 320. Inserter lower half 450 is advanced towards implant 320 whereby dovetail guides 386 and 385 of implant 320 are engaged by lower dovetail channel 452 on inserter 430 thereby securing implant 320 to inserter 430.

Figure 16:
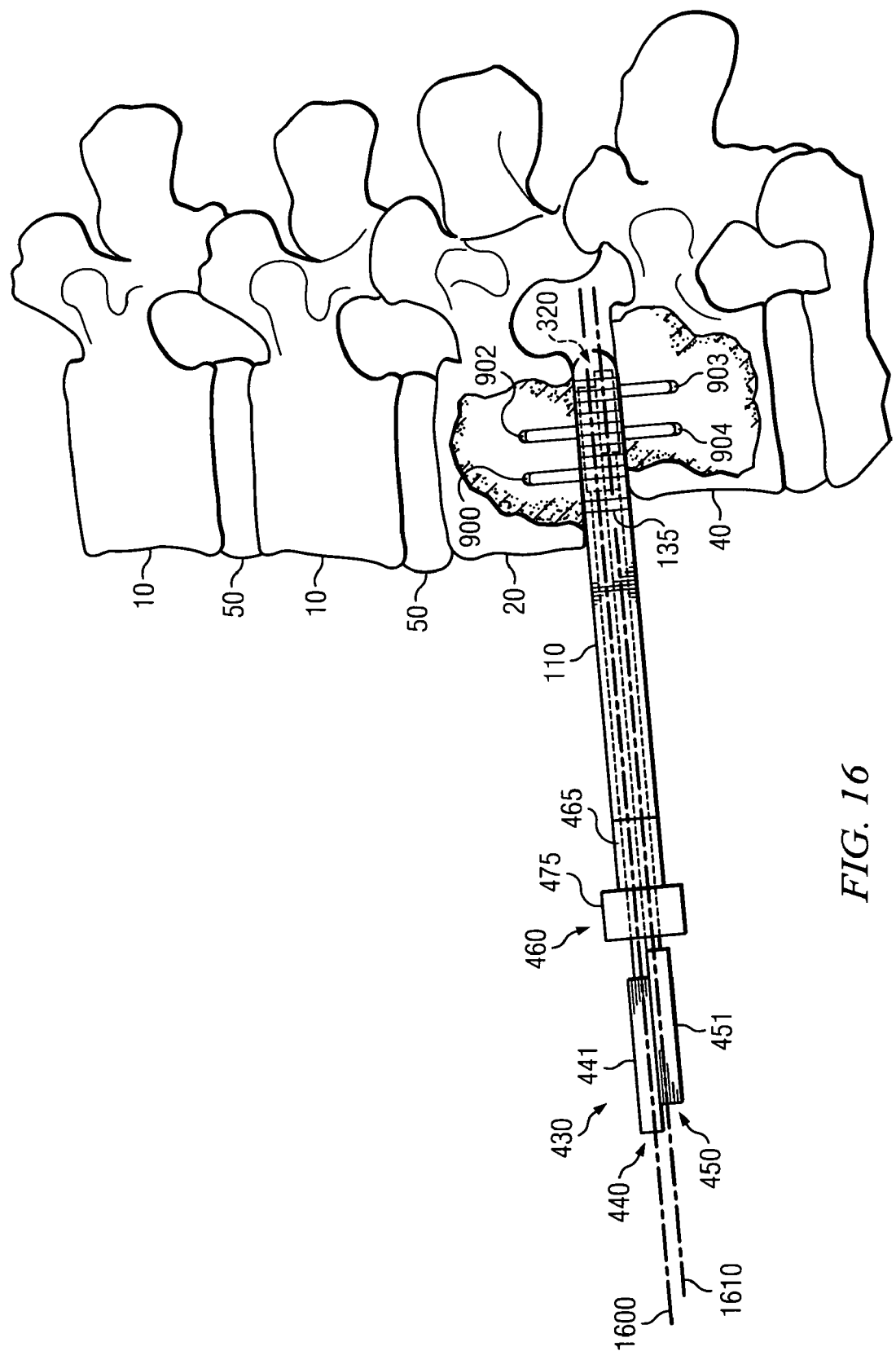
FIG. 16 is a cut away side view of a section of a human spine and an implant during positioning by an inserter of a preferred embodiment of the invention.

Referring now to FIG. 16, the process of inserting implant 320 into the affected vertebra will be described. As previously described, distractor 110 is in position between superior vertebra 20 and inferior vertebra 40. Implant 320, while attached to inserter 430 is oriented and placed within distractor channel 115. Implant 320 is placed in distractor channel 115 with radial anchors 264 and 261, 370 and 371 positioned so that clockwise rotation of the implant will result in radial anchor 264 and 261 encountering superior vertebra 20 and radial anchor 370 and 371 encounter inferior vertebra 40. Using the hexagonal section of inserter 430, implant 320 is advanced within distractor channel 115 a sufficient distance to allow guide block bottom 465 to be inserted into distractor channel 115. Guide block bottom 465 is advanced within distractor channel 115 until guide block top abuts anterior end 111 of distractor body 99.

Implant 320 is then advanced within distractor channel 115 until the hexagonal section of inserter 430 abuts guide block top 475.

The dimensions of guide block top 475 and cylindrical section of inserter 430 are such that when the hexagonal section of the inserter abuts guide block top 475, implant 320 is in proper position in relation to slots 900, 902, 903 and 904 such that radial anchor 264 is adjacent slot 900, radial anchor 261 is adjacent slot 902, radial anchor 370 is adjacent slot 904 and radial anchor 371 is adjacent slot 903.

Inserter 430 is then rotated 90 degrees clockwise such that the radial anchors are rotated into position in the slots in their respective vertebrae.

Once in position, implant 320 is released from inserter 430.

The diameter of inserter guide hole 470 should provide sufficient clearance for rotation and transition of cylindrical portion of inserter 430 without excessive play. In the preferred embodiment, the diameter of guide hole 470 should not exceed the diameter of the cylindrical section of inserter 430 by more than 0.1 mm.

To release implant 320 from inserter 430, inserter lower half 450 is retracted anteriorly past superior locking thread 445 and disengages from lower dovetail channel on lower cylindrical section 453 of the inserter. Inserter 430 is rotated 180 degrees such that upper threaded collar 345 is disengaged from locking thread 445 on implant channel 446 on the inserter. Inserter 430 and guide block 460 are then removed from distractor 110.

Distractor 110 is then removed from between superior vertebra 20 and inferior vertebra 40 by pulling anteriorly.

Figure 17:
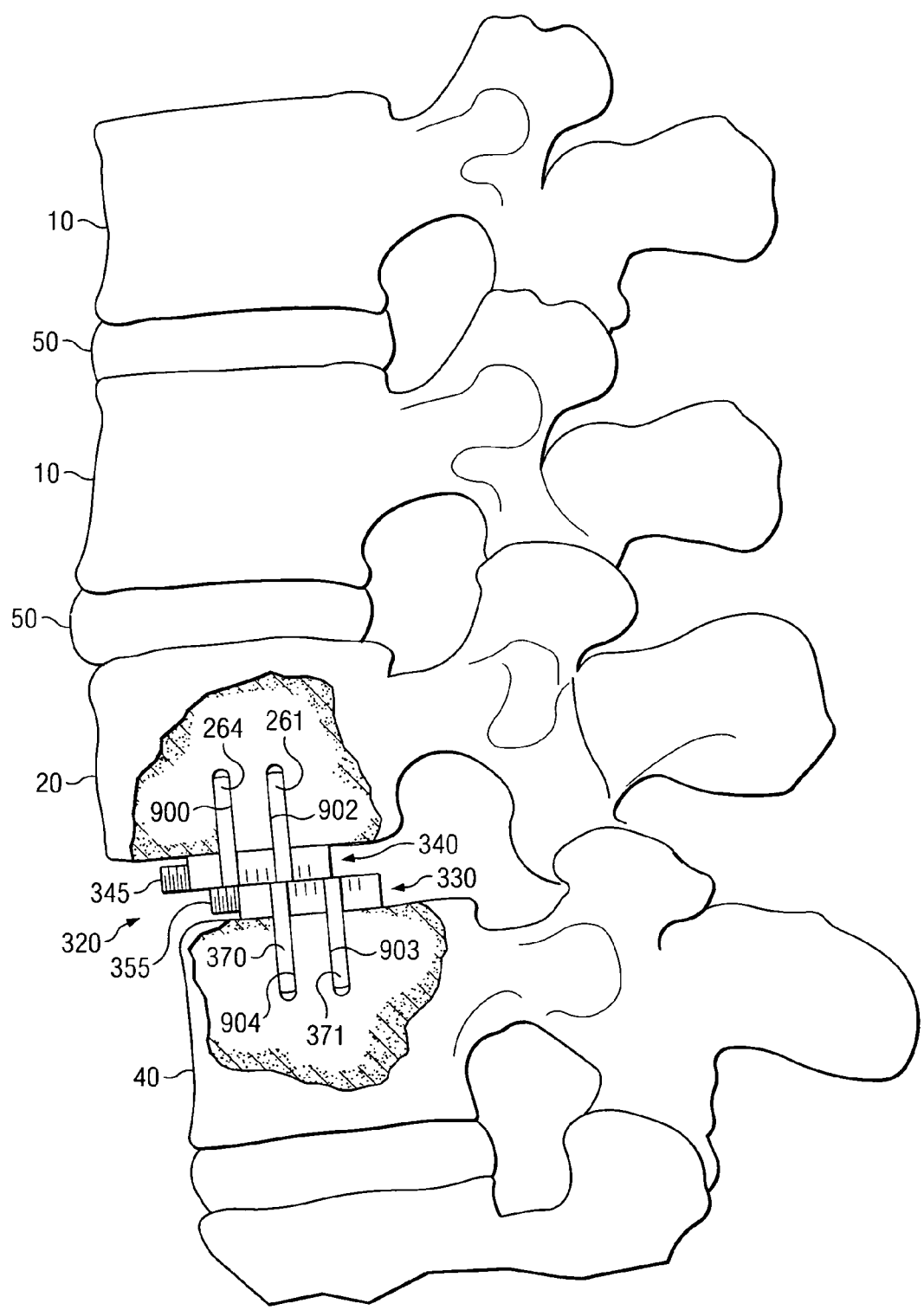
FIG. 17 is a cut away side view of a section of a human spine and an implant in place prior to the alignment of the vertebrae.

FIG. 17 illustrates the positioning of implant 320 between superior vertebra 20 and inferior vertebra 40 after distractor 110 has been removed. Upper half 340 is adjacent superior vertebra 20, radial anchor 264 is located in slot 900, radial anchor 261 is located in slot 902. Lower half 330 is adjacent inferior vertebra 40 and radial anchor 370 is located in slot 904. Radial anchor 371 is located in slot 903.

In order to align superior vertebra 20 and inferior vertebra 40, upper half 340 and lower half 330 are aligned. A spanner is inserted into spanner slot 405 of implant 320. Set screw 350 is rotated to move lower implant half 330 anteriorly and upper implant half 340 posteriorally. In one embodiment, for each complete 360 degrees turn of the set screw will move lower half 330 1 mm with respect to upper when alignment of the implant halves is complete, the threads in upper threaded collar 345 and in lower threaded collar 355 will align. Ideally, alignment of the implant halves will align the vertebrae.

After alignment of the vertebrae, an interbody arthrodesis is performed on each side of implant 320 and between remaining distended disk 70. The technique for interbody arthrodesis is surgeon's choice from those known techniques.

Figure 19B:
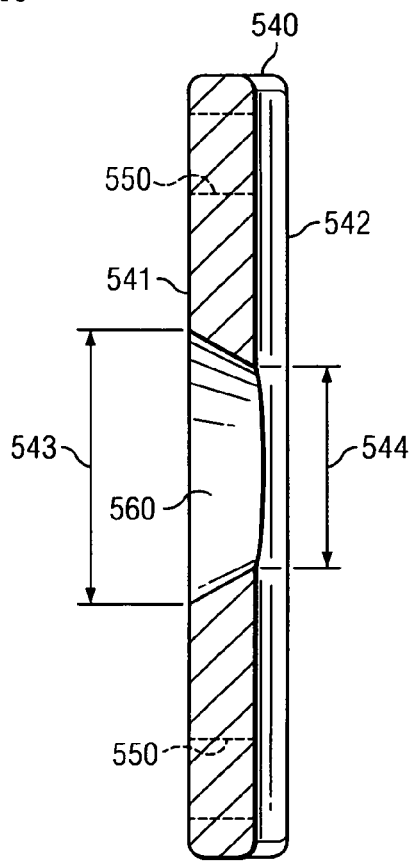
FIG. 19b is a cut away side of a plate of a preferred embodiment of the invention.
Figure 19A:
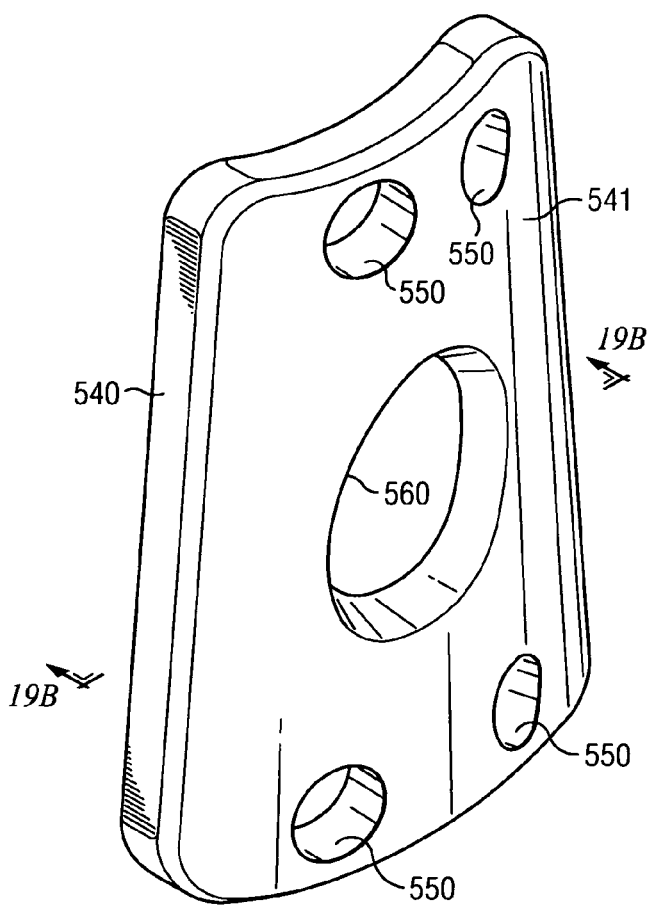
FIG. 19a is an isometric view of a plate of a preferred embodiment of the invention.

FIGS. 19a and 19b illustrates one embodiment of plate 540. Plate 540 is selected based on shape and size of individual patient's vertebrae. In one embodiment, the height of plate 540 is between 2.5 cm and 7 cm and the width of plate 540 is between 1.5 cm and 5 cm. Depth of plate 540 is between 0.2 cm and 1.5 cm. Plate 540 has front surface 541 facing an anterior side and back surface 542 facing a posterior side where back surface 542 is slightly concave to approximate the curvature of inferior vertebra 40 and superior vertebra 20.

Plate 540 includes plate nut hole 560 in its approximate center. The front diameter 543 of plate nut hole 560 on the anterior side of plate 540 is between 0.65 cm and 3.4 cm while the back diameter 544 of plate nut hole 560 on the posterior side of plate 540 is between 0.45 cm and 2.5 cm.

Plate 540 also includes four holes 550. Each hole 550 should have diameter between about 1 mm and about 9 mm. But these diameters can vary. The plate is secured to the vertebra by stainless steel screws as known in the art.

Preferably, plate 540 should be made of titanium or stainless steel.

Figure 18:
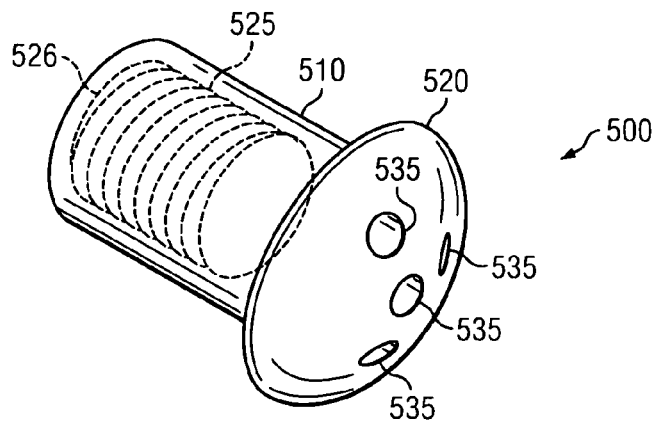
FIG. 18 is an isometric view of a nut of a preferred embodiment of the invention.

FIG. 18 illustrates one embodiment of nut 500. Nut 500 has nut head 520 which is elliptical. Diameter of nut head 520 is between 0.65 cm and 3.4 cm preferably. Nut head 520 contains spanner holes 535. Nut body 510 has diameter of between 0.5 cm and 2.5 cm. The diameter of nut body 510 should be approximately the same as diameter of implant body 346. The length of nut body 510 is between 0.2 cm and 6 cm. Nut 500 should be construction of titanium or stainless steel. Other rigid materials can be used. Nut body 510 includes threaded hole 526. Threaded hole 526 is threaded to match the threads of upper threaded collar 345 and lower threaded collar 355 on implant 320.

Figure 20:
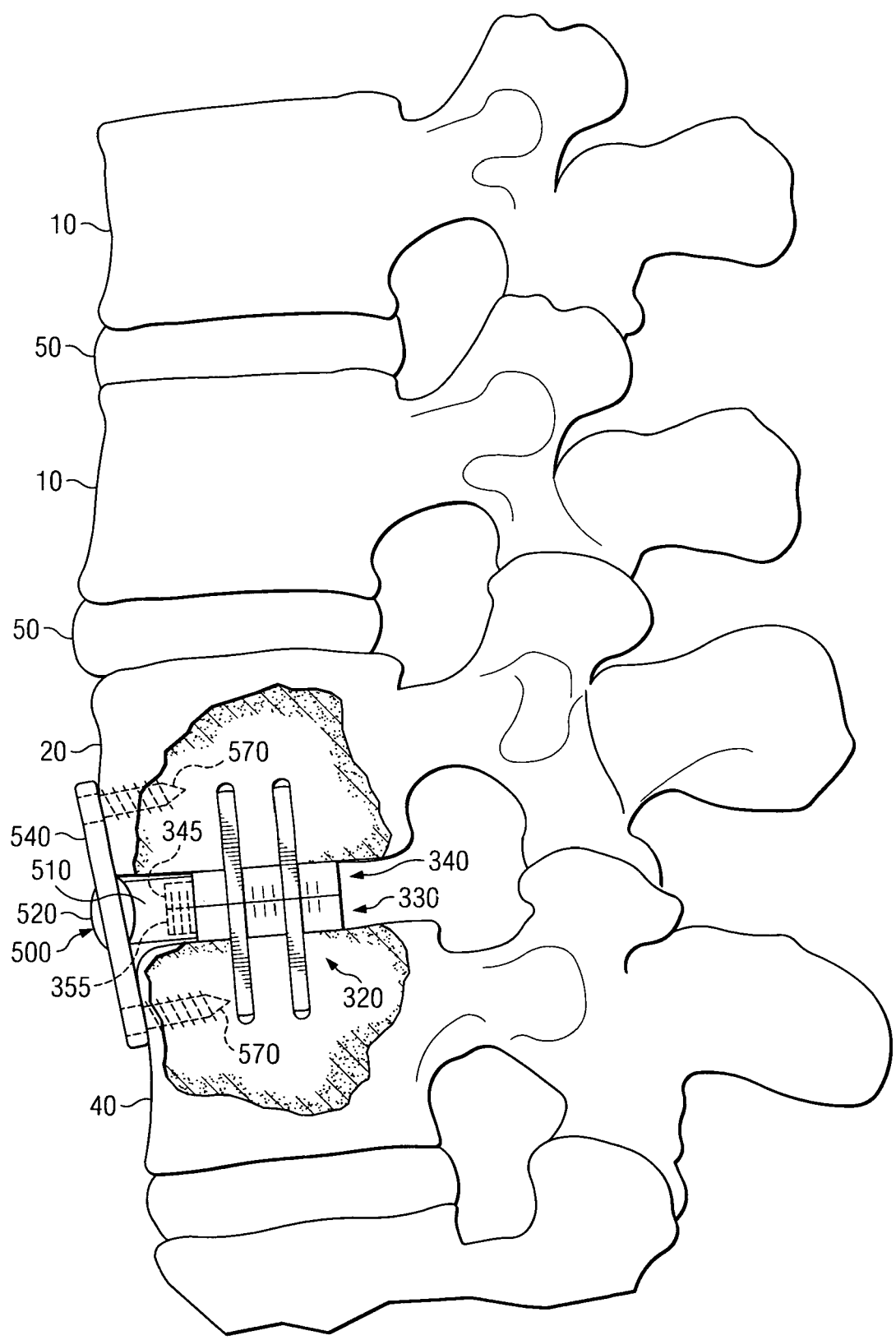
FIG. 20 is a cut away side view of a section of a human spine with an implant in a retracted position and a nut and a bolt in place.

In use, to help secure implant 320 in position, nut 500 and plate 540 are used, as illustrated in FIG. 20. Nut body 510 is placed through plate nut hole 560. Nut thread 525 of threaded hole 526 is then aligned with and threaded onto upper threaded collar 345 and lower threaded collar 355. Nut 500 prevents implant upper half 340 and implant lower half 330 from moving horizontally against each other.

Plate 540 is then properly aligned with the shape of superior vertebra 20 and inferior vertebra 40. Corticocancellous screws 570 are placed into each of the plate screw holes 550 and screwed into the respective vertebrae by traditional techniques within the field. The difference in diameters between plate nut hole 560 from front surface 541 to back surface 542 allows articulation of the bolt with respect to the plate, with front diameter 543 preferably larger than back diameter 544. Once plate 540 is attached to superior vertebrae 20 and inferior vertebrae 40 with screws 570, and is secured via nut 500 to implant 320 the device acts as a monolithic structure preventing rotational, lateral or anterior/posterior movement of vertebral bodies 20 and 40 with respect to each other, allowing ossification of said vertebral bodies.

Surgery is completed by standard anterior approach surgery techniques and implant is in place.

In the event that adjustments need to be made to implant 320, screws 570, nut 500 and plate 540 can be removed and set screw 350 adjusted with any appropriate spanner head wrench. Nut 500, plate 540 and screws 570 are then replaced.

Figure 21:
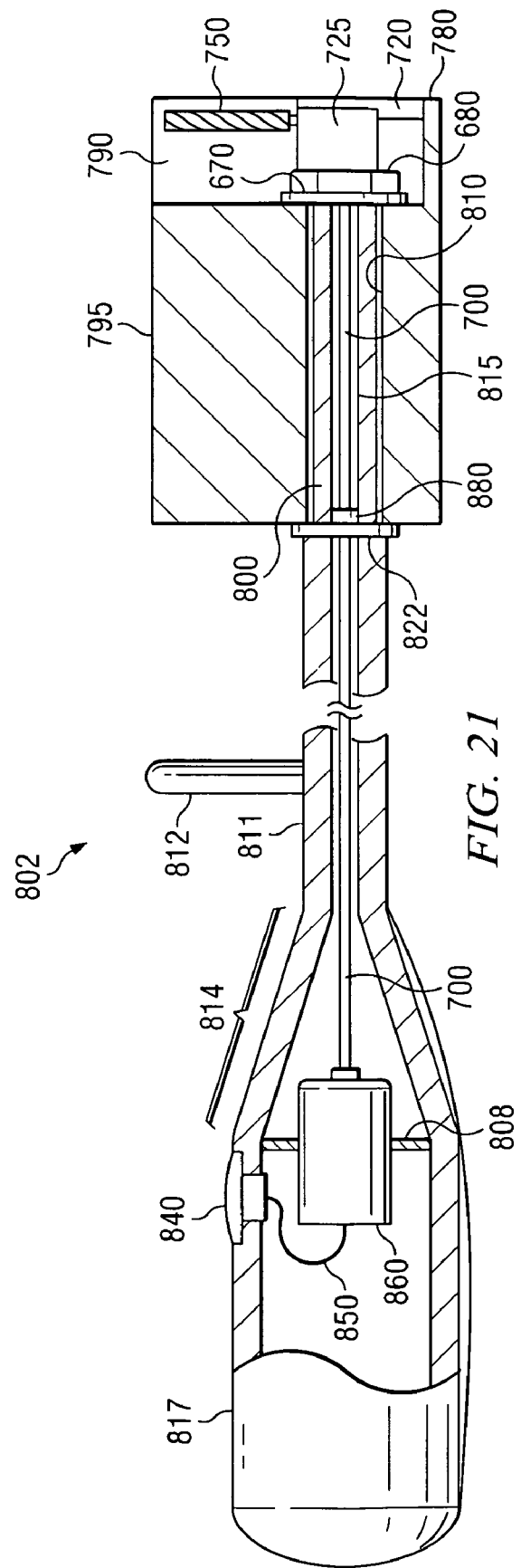
FIG. 21 is a cut away side view of a saw in an alternate saw embodiment.
Figure 22A:
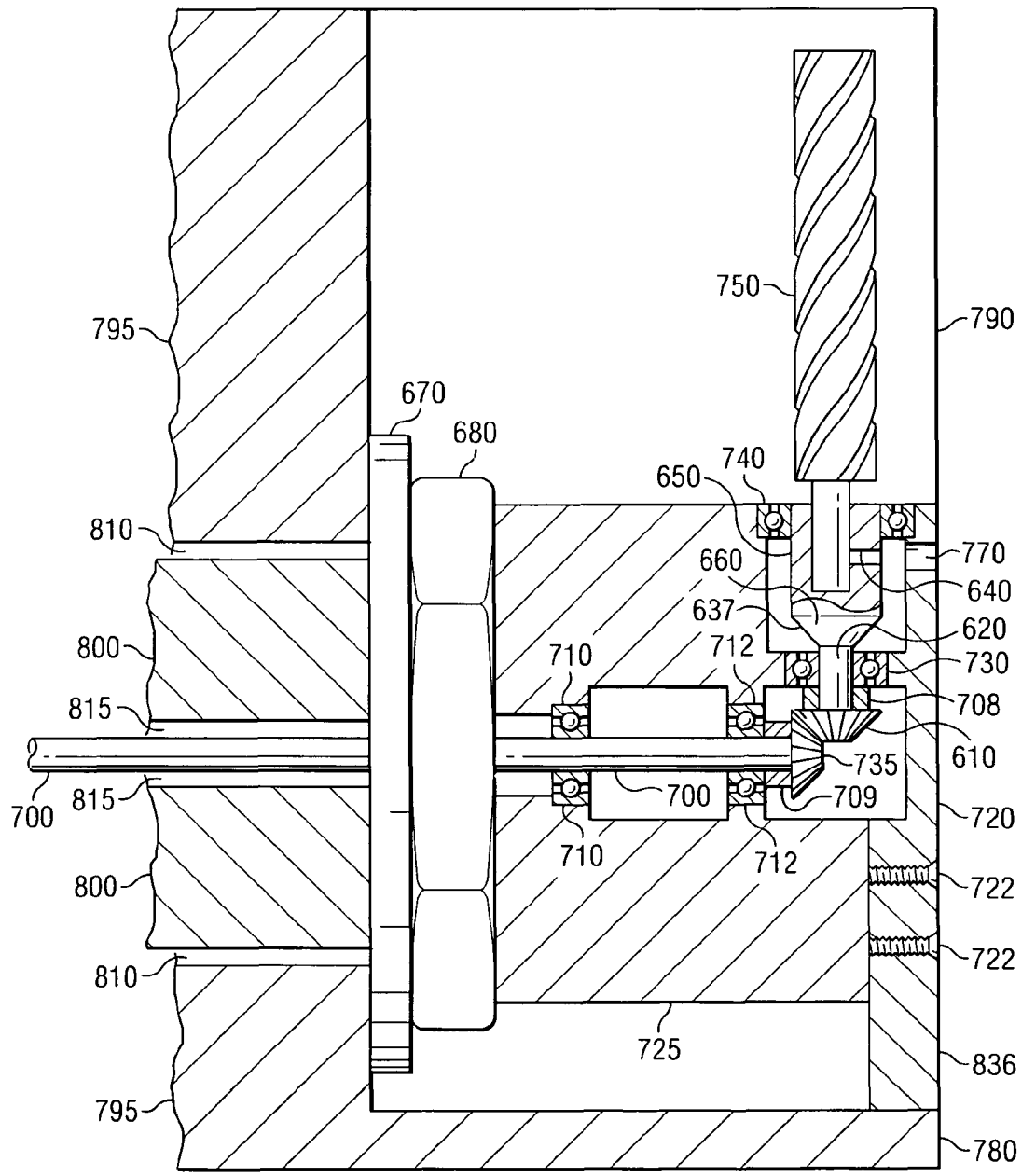
FIG. 22a is a cut away side view of the end of saw in an alternate embodiment of the invention.
Figure 22B:
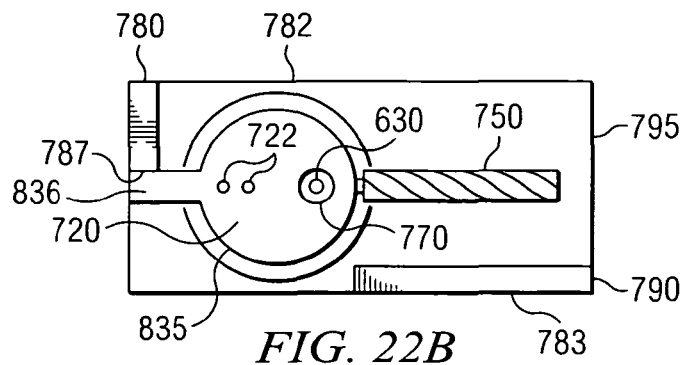
FIG. 22b is an end view of the end of an alternate saw embodiment.

FIGS. 21, 22a and 22b illustrate another preferred embodiment of the saw. FIG. 21 shows saw 802 with mill bit 750. Saw 802 includes handle 817 and conical section 814. Interior of handle 817 includes motor 860. Motor 860 is attached to mounting frame 808. Motor 860 is connected to transmission shaft 700. Switch 840 is integrated into handle 817 and is connected to motor 860 through wire 850. Switch 840 activates and deactivates motor 860. Motor 860 is connected to power source such as a rechargeable lithium ion battery or another renewable power supply as known in the art.

Motor 860 rotates transmission shaft 700 between 15,000 to 20,000 rpm. In another preferred embodiment, motor 860 has variable speeds and speed of motor 860 is modulated through use of switch 840.

Conical section 814 is connected to handle post 811. Handle post 811 integrally supports saw guide post 812. Saw guide post 812 is perpendicular to the longitudinal axis of saw 802. Handle post 811 is rigidly attached to spindle shaft 800. Shoulder 822 is positioned between handle post 811 and guide body 795. Guide body 795 is free to rotate with respect to handle post 811 and spindle shaft 800.

Transmission hole 815 extends through handle 817, conical section 814, handle post 811 and spindle shaft 800.

Transmission shaft 700 extends through transmission hole 815. Transmission shaft 700 is kept in position within transmission hole 815 by bushings 880. Transmission shaft 700 extends beyond spindle shaft 800 and into transmission housing 725.

Guide body 795 has spindle hole 810 which transverses the longitudinal axis of guide body 795. Spindle shaft 800 fits within spindle hole 810. Spindle hole 810 allows rotation of spindle shaft 800 about the longitudinal axis of guide body 795. Transmission shaft 700 extends through washer 670 and nut 680 into transmission housing 725.

FIG. 22a illustrates the mechanics inside transmission housing 725. Bearings 710 and 712 maintain position of transmission shaft 700 within transmission housing 725 while allowing it to rotate. Transmission shaft 700 terminates in bevel gear 735. Thrust bushing 709 is affixed between bevel gear 735 and bearing 712 and constrains the axial movement of transmission shaft 700. Bevel gear 735 meshes with bevel gear 610 creating 90 degree transmission. Other transmission schemes, such as a flexible cable, will suffice in other embodiments.

Bevel gear 610 is rigidly integrally connected to bearing shaft 620. Bearing shaft 620 is rigidly integrally connected to frustroconical section 637 which is rigidly integrally connected to jaws 650 of chuck 660. Mill bit 750 is inserted into jaws 650. The position of chuck 660 with respect to transmission housing 725 is maintained by bearings 740 and 730 and thrust bushing 708. Mill bit 750 is parallel to saw guide post 812.

Figure 23A:
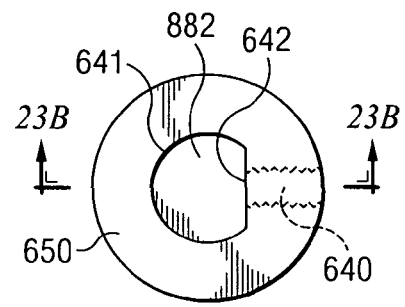
FIG. 23a is a top view of the top of the chuck of an alternate saw embodiment.
Figure 23B:
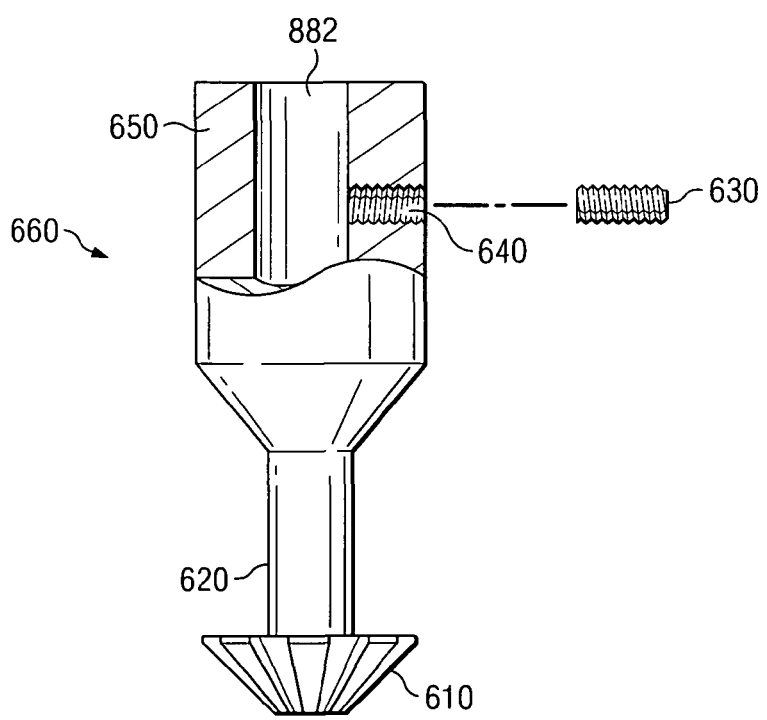
FIG. 23b is a partial cut away side view of the chuck of an alternate saw embodiment.

FIGS. 23a and 23b are further illustrations of chuck 660. Bevel gear 610 is integrally connected to bearing shaft 620. Bearing shaft 620 is integrally connected to jaws 650. Jaws 650 are approximately cylindrical in shape with mill bit hole 882 removed which is same shape as end of mill bit 750. Jaws 650 have set screw hole 640. Set screw hole 640 is threaded to mate with set screw 630.

In one embodiment, mill bit hole 882 has flat surface 642 and semicircular surface 641. Set screw hole 640 is centered along the latitudinal axis of flat surface 642.

Referring to FIGS. 22a and 22b, mounting plate 720 is attached to transmission housing 725 through use of screws 722. Mounting plate 720 has set screw hole 770. Set screw hole 770 allows access to set screw 630 for locking mill bit 750 into chuck 660. Mounting plate 720 has bit stop 836 and mounting bracket 835.

Referring now to FIG. 22b, guide body 795 includes horizontal stop 780 and vertical stop 790. Horizontal stop 780 extends from top 782 of guide body 795 and has horizontal surface 787. Vertical stop 790 is aligned with bottom 783 of guide body 795. Vertical stop 790 and horizontal stop 780 cooperate with bit stop 836 to limit the rotation of the transmission housing and the mill bit to 90 degrees between a vertical position and a horizontal position.

When handle 817 is turned counter-clockwise with respect to the longitudinal axis of guide body 795, bit stop 836 is rotated counterclockwise until bit stop 836 abuts saw guide vertical stop 790. Mill bit 750 will be substantially perpendicular to guide body 795 when bit stop 836 abuts guide vertical stop 790. When handle 817 is rotated clockwise with respect to the longitudinal axis of guide body 795, bit stop 836 will rotate clockwise until bit stop 836 abuts horizontal stop 780. When bit stop 836 abuts horizontal stop 780, mill bit 750 will be substantially parallel to guide body 795.

In use, mill bit 750 is inserted into mill bit hole 882. Set screw 630 is advanced through set screw hole 770, into set screw hole 640 until abuts mill bit 750. Saw 802 is then inserted into a distractor as described in previous embodiment. Switch 840 activates motor 860 by connecting it to a power source, which rotates transmission shaft 700 and bevel gear 735. Rotation of bevel gear 735 rotates bevel gear 610 and chuck 660, which causes mill bit 750 to rotate. Handle 817 is manually rotated counterclockwise around the longitudinal axis of guide body 795 which rotates mill bit 750 in relation to the longitudinal axis of guide body 795 and exposing mill bit 750 to vertebrae in order to cut a slot in the vertebra. After a slot has been cut, handle 817 is manually rotated clockwise around the longitudinal axis of guide body 795 until mill bit 750 is substantially parallel to latitudinal axis of guide body 795. Switch 840 then deactivates motor 860. The procedure is repeated for cutting additional slots in vertebra as previously described with manual saw embodiment.

Mill bit 750 has a diameter of between approximately 1 mm and 5 mm and a length of between 0.6 cm and 3.9 cm and corresponds to the size of the radial anchors of the implant being inserted between vertebra. Multiple size mill bits are included and the appropriate size is inserted to correspond to size needed for the particular implant.

In some spondylolisthesis conditions, the relocation of vertebra may either be minor or unnecessary, however the natural tilt and location between two adjacent vertebrae needs to be maintained and stabilized. For this type of condition, another embodiment of an implant and instrumentation are used which includes a tapering to match the tilt of the vertebrae.

Figure 24A:
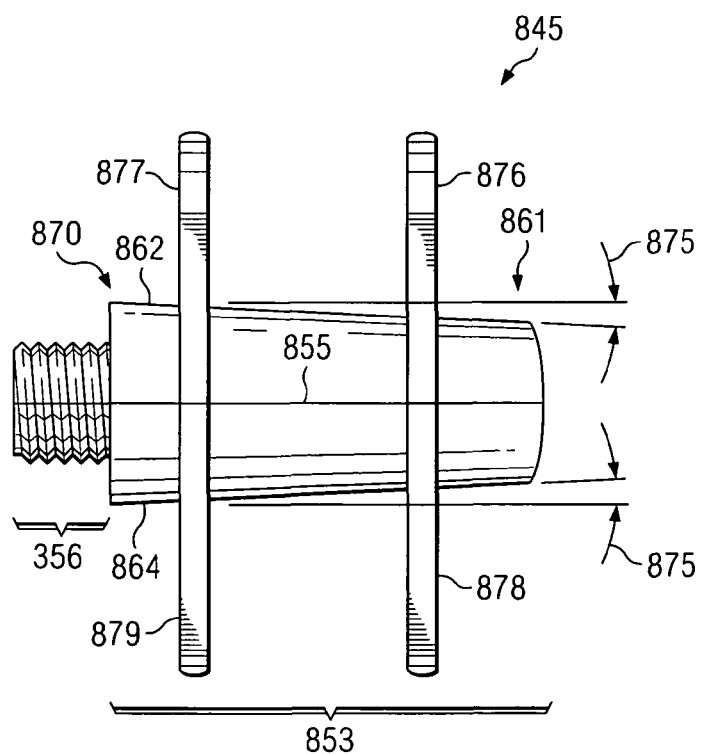
FIG. 24a is a side view of an implant in another embodiment of the invention.
Figure 24B:
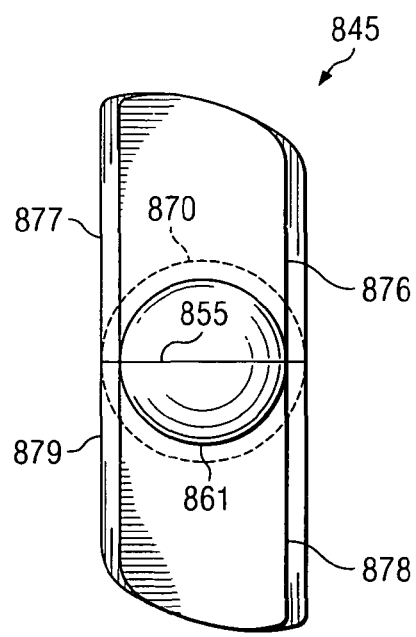
FIG. 24b is an end view of an implant in another embodiment of the invention.

FIGS. 24a and 24b are illustrative of an additional preferred embodiment of a tapered implant. Implant 845 has an implant body 853 that is tapered creating a frustroconical shape. Implant body 853 has implant body front end 870 and back end 861. The cross-section of front end 870 is circular. The cross-section of back end 861 is circular. Degree of tapering 875 is the degree by which the tapering occurs along implant body 853 and ranges between approximately 2 and 10 degrees.

Implant body 853 has two halves, upper half 862 and lower half 864. Upper half 862 and lower half 864 meet at implant seam 855.

Figure 25:
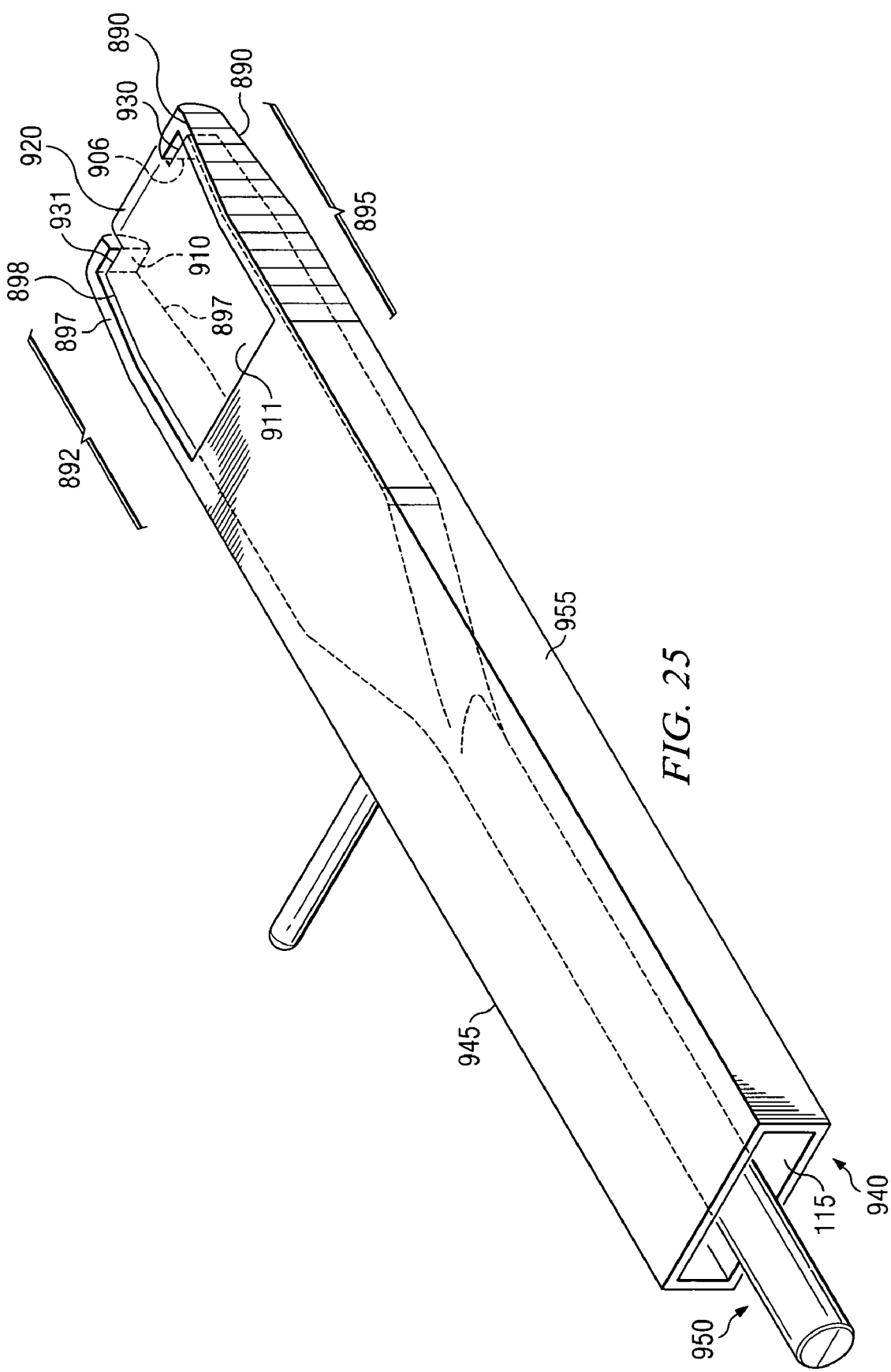
FIG. 25 is an isometric view of an impactor in conjunction with a distractor of another embodiment of the invention.

Implant body 853 has radial anchors 876 and 877 on upper half 862 and radial anchors 878 and 879 on lower half 864. Radial anchors 876, 877, 878, and 879 are substantially perpendicular to implant seam 855. Radial anchors 878 and 876 have less surface area than radial anchors 877 and 879, and are reduced in area to conform to a modified distractor as shown in FIG. 25. Other features of implant 845 are similar to those previously described in other embodiment.

FIG. 25 is illustrative of other preferred embodiments for a distractor and impactor to be used with tapered implant 845. FIG. 25 illustrates impactor 950 within distractor 940.

Distractor 940 has distractor arm 895 and distractor arm 892. Distractor arm 895 extends longitudinally from side 955 of distractor 940. Distractor arm 892 extends longitudinally from side 945 of distractor 940. Distractor arm 895 has taper arm 890 which tapers both the top and bottom between an approximate 2 and 10 degree angle along the longitudinal axis of distractor arm 895. Taper arm 897 on distractor arm 892 tapers the height from both the top and the bottom between an approximate 2 and 10 degree angle. Taper arm 897 includes distractor stop 910 and taper arm 890 has distractor stop 906. The remaining features of distractor 940 are consistent with previously disclosed embodiment of distractor.

Impactor 950 has impactor head 911. The posterior end of impactor head 911 has tapered end 898. Tapered end 898 has between approximately 2 and 10 degrees of taper along the longitudinal axis of impactor head 911. Tapered end 898 ends in impactor seat 920 and on either side of impactor seat 920 are stop surfaces 930 and 931. The tapering of tapered end 898 corresponds to the tapering of taper arm 890 and taper arm 897 such that stop surfaces 930 and 931, when fully inserted, touch distractor stop 906 and distractor stop 910 and do not extend beyond edges of distractor arms 892 or 895. The remaining features of impactor 950 are consistent with previously disclosed embodiment of impactor.

As disclosed with prior embodiments, with the tapered implant system, the implant, distractor, impactor, and other parts necessary to complete the disclosed surgery have a variety of heights depending on the patient and the condition to be resolved.

The invention claimed is:

1. A system for correcting alignment between two vertebrae caused by spondylolisthesis comprising:
    a distractor having a distractor body with a hollow channel along a distractor body longitudinal axis, an anterior end, a posterior end having first a first distractor arm and a second distractor arm which extend from the distractor body in the direction of the distractor body longitudinal axis, the first distractor arm extending parallel to the distractor body longitudinal axis having a first distractor stop surface perpendicular to the distractor body longitudinal axis, the second distractor arm extending parallel to the distractor body longitudinal axis having second distractor stop surface perpendicular to the distractor body longitudinal axis, a gap between the first distractor stop surface and the second distractor stop surface, a measurement scale along the first distractor arm, and a torque handle perpendicularly attached to the distractor body;
    an impactor having an impactor handle, an impactor body having an impactor longitudinal axis, an impactor latitudinal axis, an impactor body anterior end, and an impactor body posterior end, the impactor handle being centered on the latitudinal axis of the impactor body anterior end, an impactor seat centered along the latitudinal axis of the impactor body posterior end;
the impactor seat fitting within the gap on the distractor;
a gate having a gate longitudinal axis, a gate latitudinal axis, an interior channel along the gate longitudinal axis with a distractor end and a saw end, the distractor end having a distractor entrance to the interior channel and having a distractor stop, the saw end having a saw entrance to the interior channel, a top side, a bottom side, a right sidewall, a left sidewall, a first set of a guide slots extending from about the center of the right sidewall to about the center of the bottom side and parallel to the saw end, a second set of guide slots extending from about the center of the left sidewall to about the center of the top side and parallel to the saw end, a first handle guide slot at about the center of the right sidewall extending along the right sidewall from the saw end and connecting to the first set of guide slots and terminating in a first handle stop, a second handle guide slot at about the center of the left sidewall extending along the left sidewall from the saw end and connecting to the second set of guide slots and terminating in a second handle stop, the first set of guide slots having a first set spacing and the second set of guide slots having a second set spacing, the first set spacing related to the second set spacing by a third set spacing;
a saw with a saw longitudinal axis, the saw having a saw handle jointed to a spindle shaft connected to a saw blade, a saw guide body, and a saw guide post, the saw guide post joined to the handle at an angle generally perpendicular to the saw longitudinal axis, the saw guide body further having a longitudinal spindle hole coaxial with the saw longitudinal axis, the saw guide body further having a horizontal saw alignment stop and a vertical saw alignment stop, the spindle shaft rotatively mounted in the longitudinal spindle hole, the saw blade having a saw blade longitudinal axis parallel to the saw guide post and movable between a stoppage position dictated by the horizontal saw alignment stop and an operational position dictated by the vertical saw alignment stop;
an implant having a first half having a first body with a first longitudinal axis, a first threaded collar, a first channel, a first mating interconnection, a first outer surface and a first set of radial anchors, the first set of radial anchors radially extending generally perpendicularly from the first outer surface, a second half having a second body with a second longitudinal axis, a second threaded collar, a second channel, a second mating interconnection, a second outer surface and a second set of radial anchors, the second set of radial anchors radially extending generally perpendicularly from the second outer surface, the first half and the second half slidably connected by the first mating interconnection and the second mating interconnection, the first body and the second body connected to form an implant body, the first threaded collar and the second threaded collar connected to form an implant collar with a first thread pitch, the first channel and the second channel connected to form an implant channel, the first channel being threaded with a set of channel threads, a set screw having an outside perimeter and a spanner slot, the outside perimeter being threaded with a set of set screw threads, the set screw located in the implant channel, the set of channel threads in engagement with the set of set screw threads, the set of channel threads and the set of set screw threads having a pre-determined relationship to allow the first half to move a pre-determined distance in relation to the second half when the set screw is rotated a pre-determined angle of rotation, the first set of radial anchors and the second set of radial anchors being generally parallel;

an inserter having a top half and a bottom half, the top half further having a top longitudinal axis and a top mating guide along the top longitudinal axis, the top half having a first semi-cylindrical section and a first semi-hexagonal section, the bottom half having a bottom longitudinal axis and a bottom mating channel along the bottom longitudinal axis, the bottom half having a second semi-cylindrical section and a second semi-hexagonal section, the top half and the bottom half slidingly connected along the top mating guide and the bottom mating channel creating a cylindrical section and a hexagonal section, the top half having a connection end, the connection end having a threaded implant channel; the threaded implant channel having a second thread pitch;

the first thread pitch matching the second thread pitch;

a guide block having a guide block longitudinal axis, a guide block top connected to guide block bottom, and a guide hole centered through the guide block longitudinal axis;

a nut having a nut head and a nut body, the nut body being generally perpendicular to the nut head, the nut body having a threaded hole, the threaded hole having a third thread pitch;

the first thread pitch matching the third thread pitch; and a plate having a plate nut hole, a plurality of plate screw holes, and a front, a back, and the plate nut hole having a front diameter and a back diameter.

2. The system of claim 1 wherein the front diameter is larger than the back diameter.

3. The system of claim 1 wherein the first implant half further comprises a first set of alignment marks and the second implant half further comprises a second set of alignment marks and the first set of alignment marks align with the second set of alignment marks when the first set of radial anchors is parallel with the second set of radial anchors.

4. The system of claim 1 wherein the first distractor arm includes a first distractor point guide having a first rounded surface and the second distractor arm includes a second distractor point guide having a first angled surface.

5. The system of claim 1 wherein the nut head includes a set of spanner holes.

6. The system of claim 1 wherein the gate has a visual indicator indicating a gate orientation for the distractor.

7. The system of claim 1 wherein the measurement scale has a plurality of markings spaced 1 mm apart.

8. The system of claim 1 wherein the impactor handle has a centerline which is parallel to a horizontal axis of the impactor body.

9. The system of claim 4 wherein the impactor seat has a second rounded surface.

10. A system of tools for inserting an implant for correcting a spondylolisthesis condition between two affected vertebrae comprising:
a distractor having a distractor body with a hollow channel along a distractor body longitudinal axis, an anterior end, a posterior end having first a first distractor arm and a second first distractor arm which extend from the distractor body in the direction of the distractor body longitudinal axis, the first first distractor arm having a first distractor stop surface perpendicular to the distractor body longitudinal axis, the second first distractor arm having a second distractor stop surface perpendicular to the distractor body longitudinal axis, a gap between the first distractor stop surface and the second distractor stop surface, and a torque handle attached to the distractor body;

an impactor having a striking end and a posterior end;

the impactor fitting within the hollow channel of the distractor;

a gate with a gate longitudinal axis, a gate latitudinal axis, an interior channel along the gate longitudinal axis with a distractor end and a saw end, the distractor end having a distractor entrance to the interior channel and having a distractor stop, the saw end having a saw entrance to the interior channel, a top side, a bottom side, a right sidewall, a left sidewall, a first set of a guide slots extending from about the center of the right sidewall to about the center of the top side and parallel to the saw end, a second set of guide slots extending from about the center of the left sidewall to about the center of the bottom side and parallel to the saw end, a first handle guide slot at about the center of the right sidewall extending along the right sidewall from the saw end and connecting to the first set of guide slots and terminating in a first handle stop, a second handle guide slot at about the center of the left sidewall extending along the left sidewall from the saw end and connecting to the second set of guide slots and terminating in a second handle stop, the first set of guide slots having a first set spacing and the second set of guide slots having a second set spacing, the first set spacing related to the second set spacing by a third set spacing;

the anterior end of the distractor fitting within the interior channel at the distractor entance but not fitting within the interior channel at the saw entrance;

a saw with a saw longitudinal axis, the saw having a handle joined to a spindle shaft connected to a saw blade, a saw guide body, and a saw guide post, the saw guide post joined to the handle at an angle perpendicular to the saw longitudinal axis, the saw guide body further having a longitudinal spindle hole coaxial with the longitudinal axis, the spindle shaft rotatively mounted in the longitudinal spindle hole, the saw blade movable between a stoppage position and an operational position;

the saw guide body fitting within the interior channel at the saw entrance of the gate and the hollow channel of the distractor;

an implant adapted to be fitted between the affected vertebrae having a first half having a first half longitudinal axis, a first half outer surface, and a first mating interconnection and a second half having a second half longitudinal axis, a second half outer surface, and a second mating interconnection, the first half and the second half connected by the first mating interconnection and the second mating interconnection forming an implant body, the first half having a first channel and the second half having a second channel such that when the first half and the second half are connected the first channel and the second channel form an implant channel in the implant body, a set screw located inside the implant chamber having a set of set screw threads, the first channel having a set of channel threads, the first half having a first set of radial anchors extending perpendicularly from the first half outer surface and the second half having a second set of radial anchors extending perpendicularly from the second half outer surface;

the set of set screw threads engaging the set of channel threads;

an inserter having a top half and a bottom half, the top half having a top longitudinal axis and a top mating guide along the top longitudinal axis, the bottom half having a bottom longitudinal axis and a bottom mating guide along the bottom longitudinal axis, the top half and the bottom half slidingly connected along the top mating guide and the bottom mating guide, the top half having a connection end, the connection end releasably connectable to the implant body;

a nut having a nut head and a nut body, the nut body being perpendicular to the nut head, the nut body having an implant hole, releasably connectable to the implant body;

a plate connectable to the two affected vertebrae having a plate hole through which passes the nut body.

11. The system of claim 10 wherein the implant body has a set of alignment marks on the first implant half and the second implant half.

12. The system of claim 10 wherein the gate has a visual indicator indicating a direction of distractor insertion.

13. The system of claim 10 wherein the distractor has a measurement scale along the first distractor arm.

14. The system of claim 10 where the impactor has an impactor handle, an impactor body having an impactor longitudinal axis, an impactor latitudinal axis, an impactor body anterior end, and an impactor body posterior end, the impactor handle being centered on the latitudinal axis at the impactor body anterior end, an impactor seat centered along the impactor latitudinal axis at the impactor body posterior end;

the impactor seat fitting within the gap on the distractor.

15. The system of claim 10 where the guide body further has a horizontal saw alignment stop and a vertical saw alignment stop.

16. The system of claim 10 further comprising a guide block having a guide block longitudinal axis, a guide block top connected to a guide block bottom, and a guide hole centered through the guide block longitudinal axis; the guide block bottom fitting into the hollow channel.

17. The system of claim 10 further comprising a set of distractors, wherein each distractor of the set of distractors has a unique height.

18. The system of claim 10 further comprising a set of impactors, wherein each impactor of the set of impactors has a unique height.

19. The system of claim 10 further comprising a set of saw guide bodies, wherein each saw guide body of the set of saw guide bodies has a unique height.

20. The system of claim 10 further comprising a set of implants, each of the set of implant bodies having a unique diameter.

\* \* \* \* \*